(12) United States Patent
Nalagatla et al.

(10) Patent No.: US 12,133,647 B2
(45) Date of Patent: Nov. 5, 2024

(54) SURGICAL STAPLER END EFFECTOR SLED HAVING CARTRIDGE WALL SUPPORT FEATURE

(71) Applicant: Cilag GmbH International, Zug (CH)

(72) Inventors: Anil K. Nalagatla, Mason, OH (US); Frederick E. Shelton, IV, Hillsboro, OH (US); Michael E. Setser, Burlington, KY (US); Geoffrey C. Hueil, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/957,320

(22) Filed: Sep. 30, 2022

(65) Prior Publication Data
US 2023/0113273 A1   Apr. 13, 2023

Related U.S. Application Data

(63) Continuation of application No. 17/088,941, filed on Nov. 4, 2020, now Pat. No. 11,540,826.

(51) Int. Cl.
A61B 17/068 (2006.01)
A61B 17/072 (2006.01)

(52) U.S. Cl.
CPC ........ A61B 17/0686 (2013.01); A61B 17/072 (2013.01); A61B 2017/07257 (2013.01);
(Continued)

(58) Field of Classification Search
CPC ............ A61B 17/0684; A61B 17/0686; A61B 17/072; A61B 17/07297; A61B 17/0644;
(Continued)

(56) References Cited

U.S. PATENT DOCUMENTS 5,285,742 A   2/1994  Anderson
5,597,107 A   1/1997  Knodel et al.
(Continued)

FOREIGN PATENT DOCUMENTS

CN   107802304 A   3/2018
EP     2997906 A1   3/2016
(Continued)

OTHER PUBLICATIONS

International Search Report and Written Opinion dated Feb. 4, 2022, for Application No. PCT/IB2021/060156, 12 pages.
(Continued)

Primary Examiner — Stephen F. Gerrity
Assistant Examiner — Linda J Hodge
(74) Attorney, Agent, or Firm — Frost Brown Todd LLP

(57) ABSTRACT

A staple driver actuator for a surgical stapler includes a base having at least one bottom surface. The bottom surface defines a plane and is configured to slide longitudinally relative to a jaw of the surgical stapler. The staple driver actuator also includes a plurality of rails extending upwardly from the base. Each of the plurality of rails includes at least one cam surface, and each of the cam surfaces is inclined relative to the plane. The plurality of rails includes a laterally-opposed pair of outer rails and a laterally-opposed pair of inner rails. The staple driver actuator further includes a distal nose extending distally from at least a portion of the base and having at least one ledge surface. The ledge surface faces upwardly, is parallel to the plane, and is at least partially positioned distally relative to each of the outer and inner rails.

16 Claims, 20 Drawing Sheets

(52) U.S. Cl.
CPC ............... *A61B 2017/07271* (2013.01); *A61B 2017/07278* (2013.01)

(58) Field of Classification Search
CPC .. A61B 2017/0688; A61B 2017/07278; A61B 2017/07271; A61B 2017/07257; A61B 2017/07264
USPC ................................ 227/176.1, 178.1, 181.1
See application file for complete search history.

(56) References Cited

U.S. PATENT DOCUMENTS

| | | | |
|---|---|---|---|
| 5,762,255 | A | 6/1998 | Chrisman et al. |
| 7,404,508 | B2 | 7/2008 | Smith et al. |
| 7,434,715 | B2 | 10/2008 | Shelton, IV et al. |
| 7,565,993 | B2 | 7/2009 | Milliman et al. |
| 7,635,074 | B2 | 12/2009 | Olson et al. |
| 7,641,091 | B2 | 1/2010 | Olson et al. |
| 7,721,930 | B2 | 5/2010 | McKenna et al. |
| 8,127,975 | B2 | 3/2012 | Olson et al. |
| 8,186,556 | B2 | 5/2012 | Viola |
| 8,210,411 | B2 | 7/2012 | Yates et al. |
| 8,257,634 | B2 | 9/2012 | Scirica |
| 8,408,439 | B2 | 4/2013 | Huang et al. |
| 8,453,914 | B2 | 6/2013 | Laurent et al. |
| 8,464,922 | B2 | 6/2013 | Marczyk |
| 8,496,154 | B2 | 7/2013 | Marczyk et al. |
| 8,657,177 | B2 | 2/2014 | Scirica et al. |
| 8,746,533 | B2 | 6/2014 | Whitman et al. |
| 8,931,683 | B2 | 1/2015 | Racenet et al. |
| 9,055,941 | B2 | 6/2015 | Schmid et al. |
| 9,186,142 | B2 | 11/2015 | Fanelli et al. |
| 9,517,065 | B2 | 12/2016 | Simms et al. |
| 9,554,796 | B2 | 1/2017 | Kostrzewski |
| 9,622,746 | B2 | 4/2017 | Simms et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,943,310 | B2 | 4/2018 | Harris et al. |
| 9,987,012 | B2 | 6/2018 | Shah |
| 10,092,292 | B2 | 10/2018 | Boudreaux et al. |
| 10,130,360 | B2 | 11/2018 | Olson et al. |
| 10,426,481 | B2 | 10/2019 | Aronhalt et al. |
| 10,433,843 | B2 | 10/2019 | Yee |
| 10,433,845 | B2 | 10/2019 | Baxter, III et al. |
| 10,478,185 | B2 | 11/2019 | Nicholas |
| 10,682,137 | B2 | 6/2020 | Stokes et al. |
| 10,898,187 | B2 | 1/2021 | Deck et al. |
| 10,939,911 | B2 | 3/2021 | Huitema et al. |
| 10,959,727 | B2 | 3/2021 | Hunter et al. |
| 10,980,539 | B2 | 4/2021 | Harris et al. |
| 10,993,716 | B2 | 5/2021 | Shelton, IV et al. |
| 11,033,266 | B2 | 6/2021 | Jones et al. |
| 11,045,196 | B2 | 6/2021 | Olson et al. |
| 11,051,812 | B2 | 7/2021 | Hopkins et al. |
| 11,134,947 | B2 | 10/2021 | Shelton, IV |
| 11,141,153 | B2 | 10/2021 | Shelton, IV et al. |
| 11,160,551 | B2 | 11/2021 | Shelton, IV et al. |
| 11,202,633 | B2 | 12/2021 | Harris et al. |
| 11,219,456 | B2 | 1/2022 | Baxter, III et al. |
| 11,246,590 | B2 | 2/2022 | Swayze et al. |
| 11,382,621 | B2 | 7/2022 | Scheib et al. |
| 11,523,821 | B2 | 12/2022 | Harris et al. |
| 2007/0075115 | A1* | 4/2007 | Olson .............. A61B 17/07207 227/176.1 |
| 2010/0006620 | A1 | 1/2010 | Sorrentino et al. |
| 2013/0098969 | A1* | 4/2013 | Scirica ............ A61B 17/07207 227/180.1 |
| 2013/0284791 | A1* | 10/2013 | Olson .............. A61B 17/07207 227/176.1 |
| 2013/0334287 | A1 | 12/2013 | Shelton, IV |
| 2014/0166726 | A1 | 6/2014 | Schellin et al. |
| 2017/0037568 | A1 | 2/2017 | Love et al. |
| 2018/0353180 | A1* | 12/2018 | Huitema .......... A61B 17/07207 |
| 2019/0076142 | A1* | 3/2019 | Wixey ................... A61B 34/37 |
| 2019/0374224 | A1 | 12/2019 | Huitema et al. |
| 2020/0046353 | A1 | 2/2020 | Deck et al. |
| 2020/0275930 | A1 | 9/2020 | Harris et al. |
| 2021/0038223 | A1 | 2/2021 | Schings et al. |
| 2021/0307743 | A1 | 10/2021 | Cappola |
| 2022/0133305 | A1 | 5/2022 | Nalagatla et al. |
| 2022/0133306 | A1 | 5/2022 | Nalagatla et al. |
| 2022/0133307 | A1 | 5/2022 | Nalagatla et al. |
| 2022/0133313 | A1 | 5/2022 | Nalagatla et al. |
| 2022/0133316 | A1 | 5/2022 | Nalagatla et al. |

FOREIGN PATENT DOCUMENTS

| | | | | |
|---|---|---|---|---|
| EP | | 3015080 | A2 | 5/2016 |
| EP | | 3305212 | A2 * | 4/2018 ......... A61B 17/0644 |
| EP | | 3636167 | A1 | 4/2020 |
| EP | | 3673831 | A2 | 7/2020 |
| JP | | 2015-196085 | A | 11/2015 |
| JP | | 2017-513593 | A | 6/2017 |
| JP | | 2019-514487 | A | 6/2019 |
| WO | WO 2019/003031 | | A1 | 1/2019 |

OTHER PUBLICATIONS

International Search Report and Written Opinion dated Feb. 7, 2022, for Application No. PCT/IB2021/060161, 16 pages.
International Search Report and Written Opinion dated Feb. 9, 2022, for Application No. PCT/IB2021/060164, 13 pages.
International Search Report and Written Opinion dated Feb. 16, 2022, for Application No. PCT/IB2021/060163, 15 pages.
International Search Report and Written Opinion dated Feb. 9, 2022, for Application No. PCT/IB2021/060162, 12 pages.
Japanese Office Action dated Jan. 18, 2022, for Application No. 2021-009457, 1 page.
Japanese Office Action dated Jan. 18, 2022, for Application No. 2021-009458, 1 page.
Japanese Office Action dated Jan. 18, 2022, for Application No. 2021-022905, 1 page.
Japanese Office Action dated Jan. 18, 2022, for Application No. 2021-022906, 1 page.
Japanese Office Action dated Jan. 18, 2022, for Application No. 2021-022895, 1 page.
Japanese Office Action dated Jan. 18, 2022, for Application No. 2021-022896, 1 page.
Design U.S. Appl. No. 29/757,203 entitled, "Surgical Stapler End Effector Sled," filed Nov. 4, 2020.
Design U.S. Appl. No. 29/757,204 entitled, "Surgical Stapler End Effector Sled," filed Nov. 4, 2020.
U.S. Appl. No. 17/895,198 entitled, "Surgical Stapler End Effector Sled Having Staple Driver Support Feature," filed Aug. 25, 2022.
U.S. Appl. No. 17/895,200 entitled, "Surgical Stapler End Effector Sled Having Staple Driver Support Feature," filed Aug. 25, 2022.

* cited by examiner

SURGICAL STAPLER END EFFECTOR SLED HAVING CARTRIDGE WALL SUPPORT FEATURE

This application is a continuation of U.S. application Ser. No. 17/088,941, entitled "Surgical Stapler End Effector Sled having Cartridge Wall Support Feature," filed Nov. 4, 2020, issued as U.S. Pat. No. 11,540,826 on Jan. 3, 2023.

BACKGROUND

Examples of surgical instruments include surgical staplers, which may be configured for use in laparoscopic surgical procedures and/or open surgical procedures. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein in its entirety.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
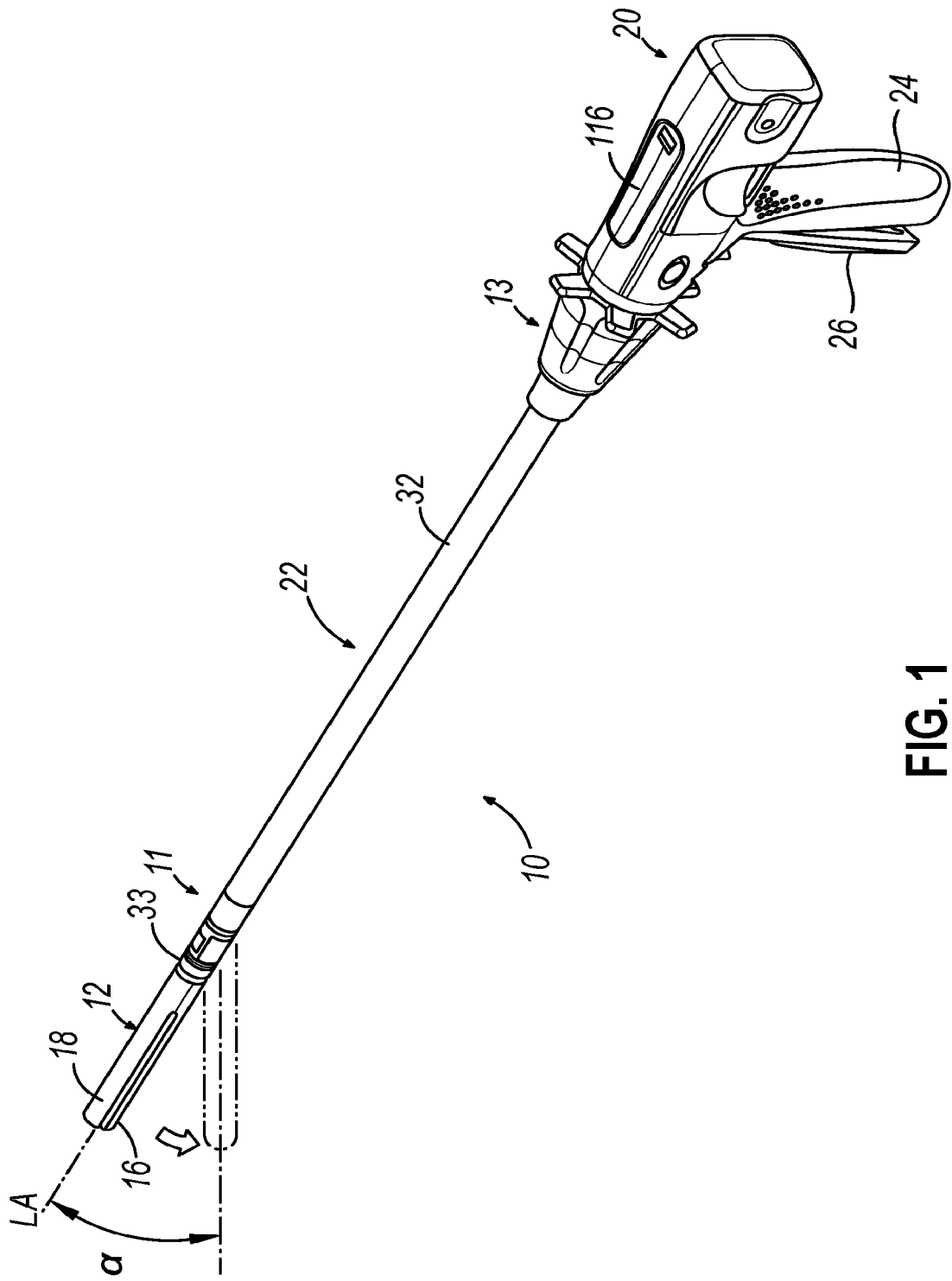
FIG. 1 depicts a perspective view of an example of an articulating surgical stapling instrument.
Figure 2:
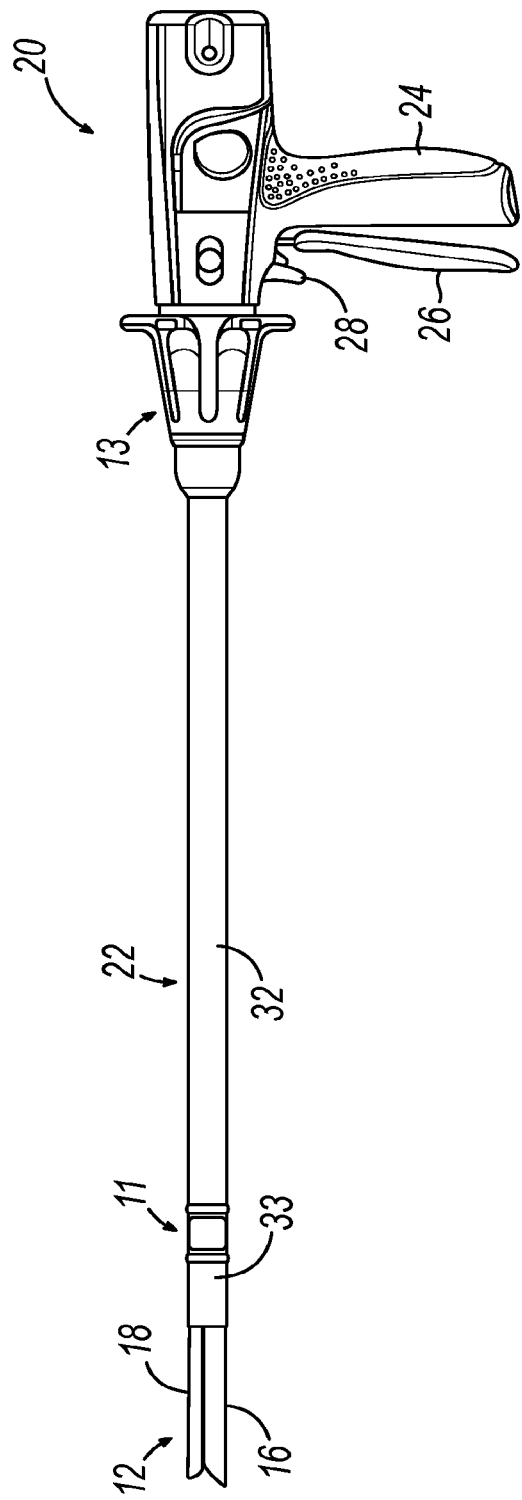
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXAMPLE OF SURGICAL STAPLER

FIGS. 1-7 depict an example of a surgical stapling and severing instrument (10) that is sized for insertion, in a nonarticulated state as depicted in FIG. 1, through a trocar cannula, thoracotomy, or other incision to a surgical site in a patient for performing a surgical procedure. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20).

Once articulation joint (11) and end effector (12) are inserted into the patient, articulation joint (11) may be remotely articulated, as depicted in phantom in FIG. 1, by an articulation control (13), such that end effector (12) may be deflected from the longitudinal axis (LA) of shaft (22) at a desired angle (a). By way of example only, articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety; and/or U.S. Pat. No. 9,795,379, entitled "Surgical Instrument with Multi-Diameter Shaft," issued Oct. 24, 2017, the disclosure of which is incorporated by reference herein in its entirety. Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). By way of example only, lower jaw (16) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (18) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of tissue clamped in end effector (12), as will be described in greater detail below. Thereafter, triggers (26, 28) may be released to release the tissue from end effector (12).

Figure 4A:
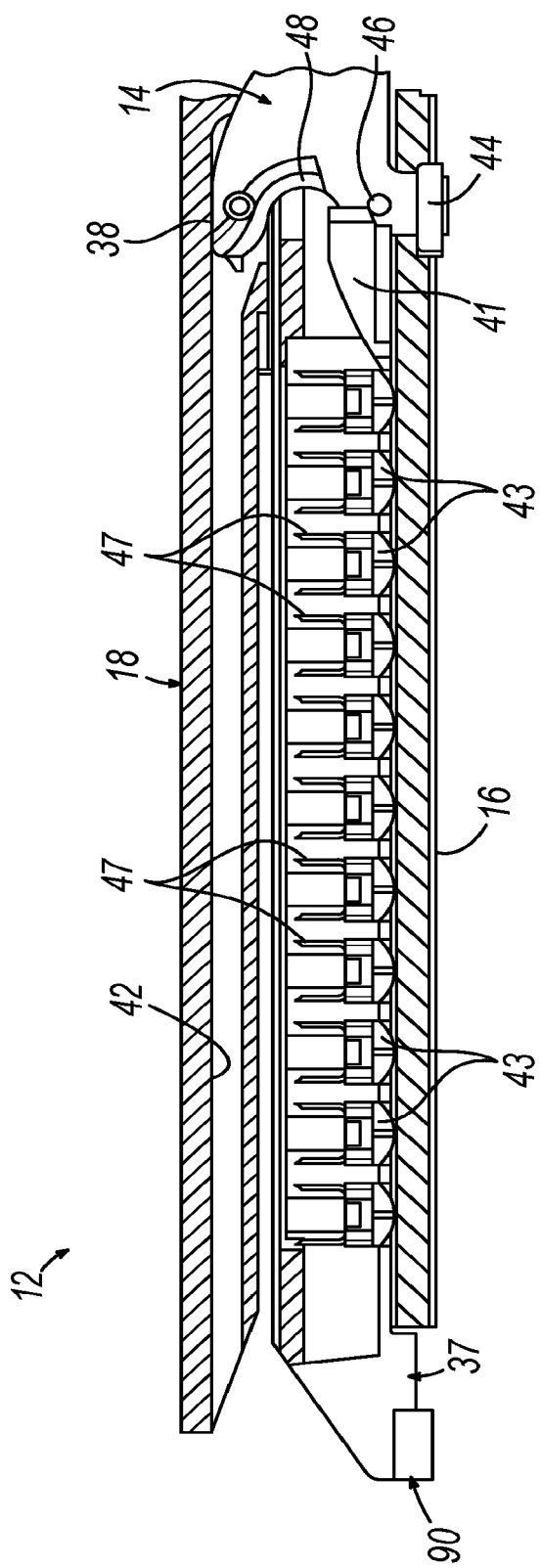
FIG. 4A depicts a side cross-sectional view of the end effector of FIG. 3, taken along line 4-4 of FIG. 3, with a firing beam in a proximal position.
Figure 4B:
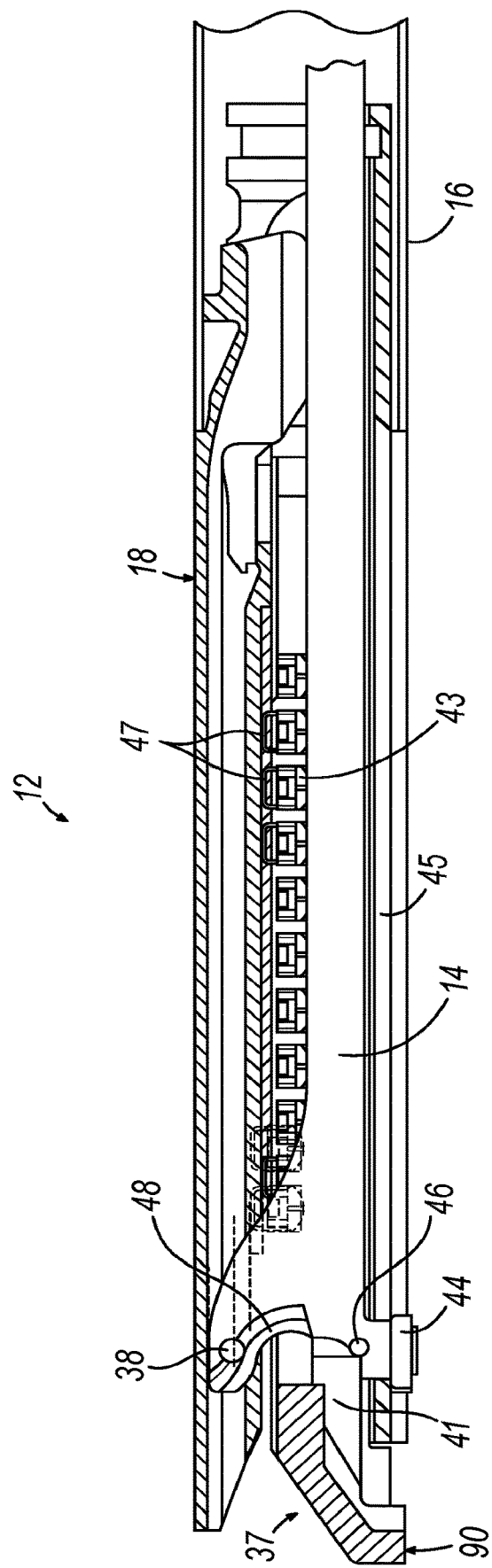
FIG. 4B depicts a side cross-sectional view of the end effector of FIG. 3, taken along line 4-4 of FIG. 3, with the firing beam in a distal position.

As best seen in FIGS. 4A-4B, firing beam (14) of the present example includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein in its entirety. Other suitable forms that firing beam (14) may take will be apparent to those skilled in the art in view of the teachings herein.

Figure 3:
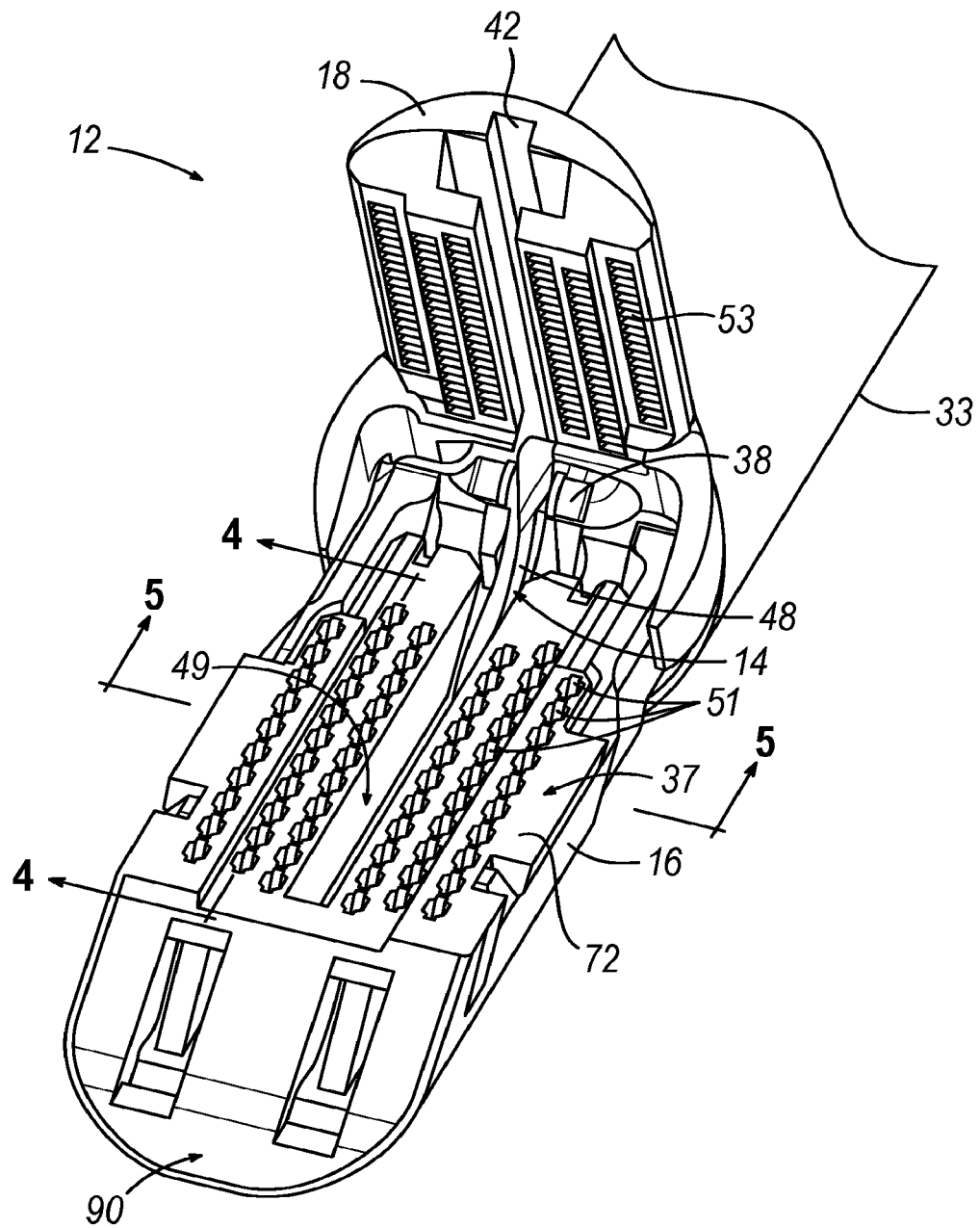
FIG. 3 depicts a perspective view of an opened end effector of the instrument of FIG. 1.
Figure 5:
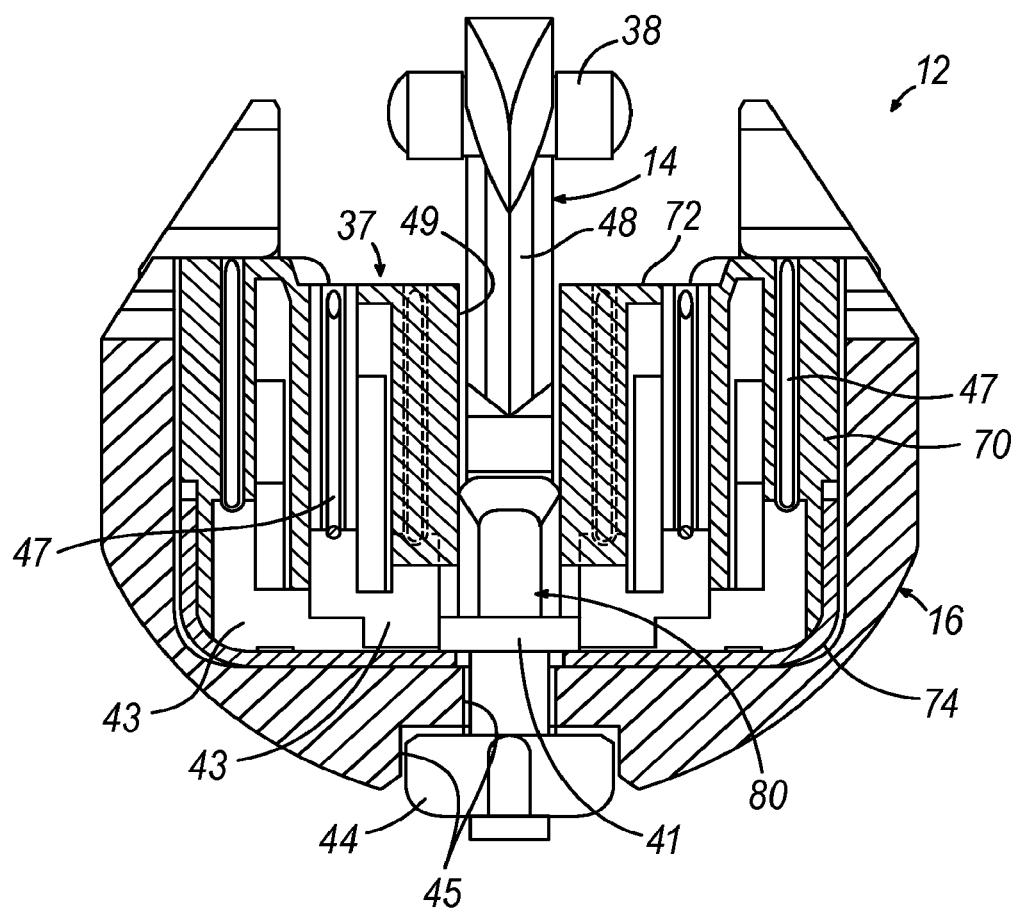
FIG. 5 depicts an end cross-sectional view of the end effector of FIG. 3, taken along line 5-5 of FIG. 3.
Figure 6:
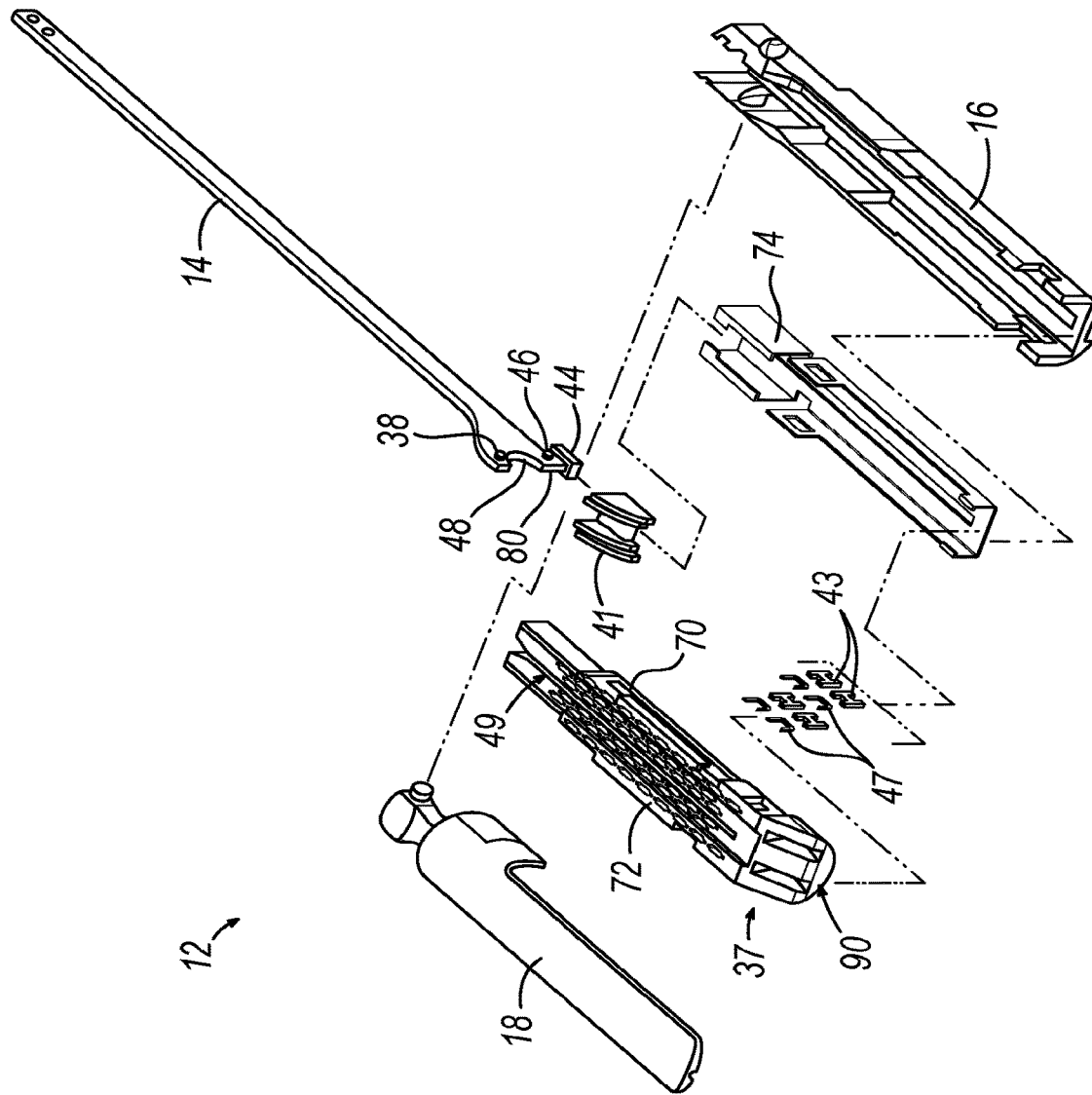
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). Three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number)

may be provided. Referring back to FIGS. 4A-6, a wedge sled (41) and a plurality of staple drivers (43) are captured between cartridge body (70) and tray (74), with wedge sled (41) being located proximal to staple drivers (43) when staple cartridge (37) is in an pre-fired (or "unspent") state. Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

By way of example only, staple cartridge (37) may be constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein in its entirety. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) located at the distal end of firing beam (14) is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
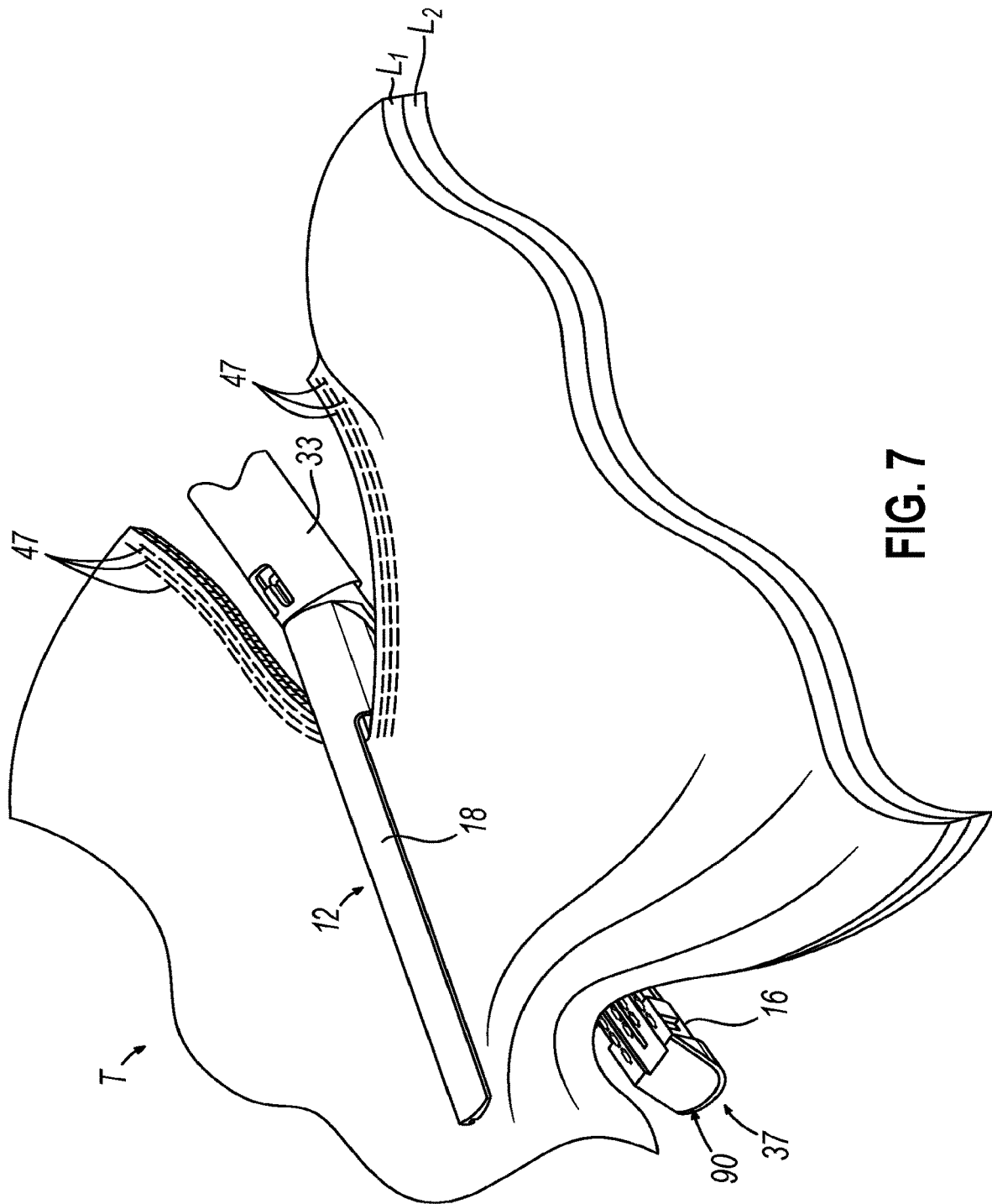
FIG. 7 depicts a perspective view of the end effector of FIG. 3, positioned at tissue and having been actuated once in the tissue.

FIG. 7 shows end effector (12) having been actuated through a single stroke through layers ($L_1$, $L_2$) of tissue (T). As shown, cutting edge (48) (obscured in FIG. 7) has cut through tissue (T), while staple drivers (43) have driven three alternating rows of staples (47) through the tissue (T) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar or incision after the first stroke is complete, spent staple cartridge (37) is replaced with a new staple cartridge, and end effector (12) is then again inserted through the trocar or incision to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

In some versions, instrument (10) provides motorized control of firing beam (14). By way of example only, such motorization may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein in its entirety; and/or U.S. Pat. No. 8,210,411, entitled "Motor-Driven Surgical Instrument," issued Jul. 3, 2012, the disclosure of which is incorporated by reference herein in its entirety. Other suitable components, features, and configurations for providing motorization of firing beam (14) will be apparent to those skilled in the art in view of the teachings herein. It should also be understood that some other versions may provide manual driving of firing beam (14), such that a motor may be omitted.

II. EXEMPLARY SLED HAVING CARTRIDGE WALL SUPPORT FEATURE AND MULTIPLE SURFACE FINISHES

Figure 8:
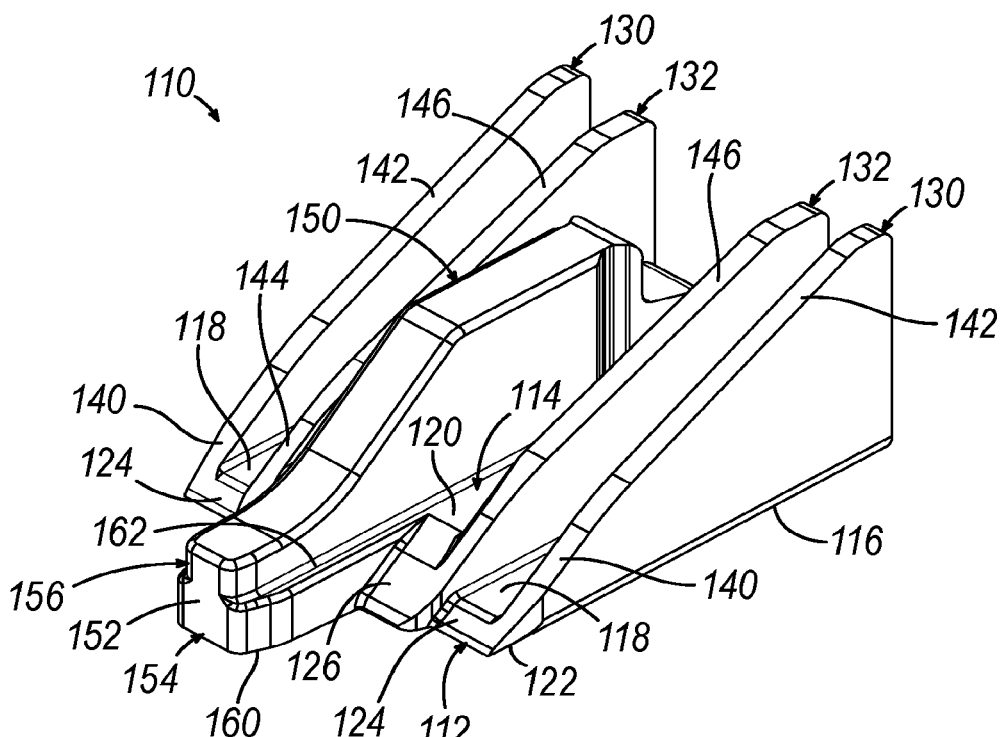
FIG. 8 depicts a perspective view of an example of a wedge sled for actuating staple drivers of the instrument of FIG. 1, showing the wedge sled having a cartridge wall support feature and multiple surface finishes.
Figure 9:
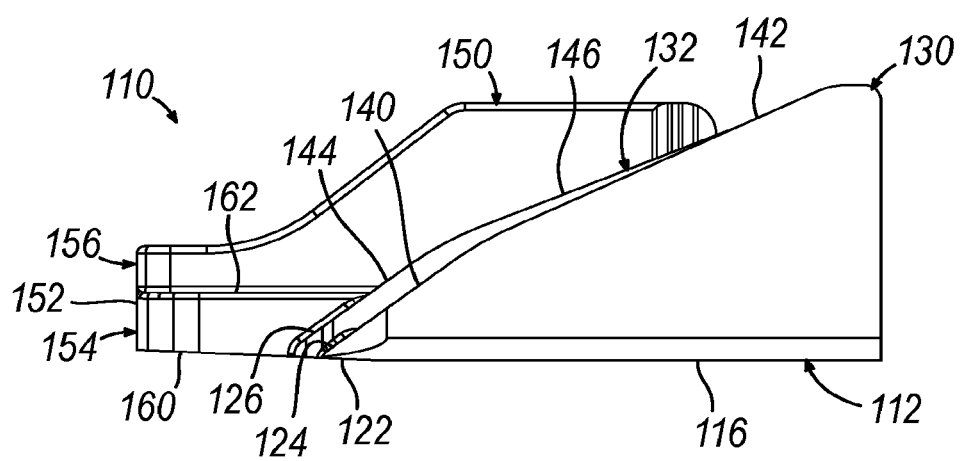
FIG. 9 depicts a side view of the wedge sled of FIG. 8.
Figure 10:
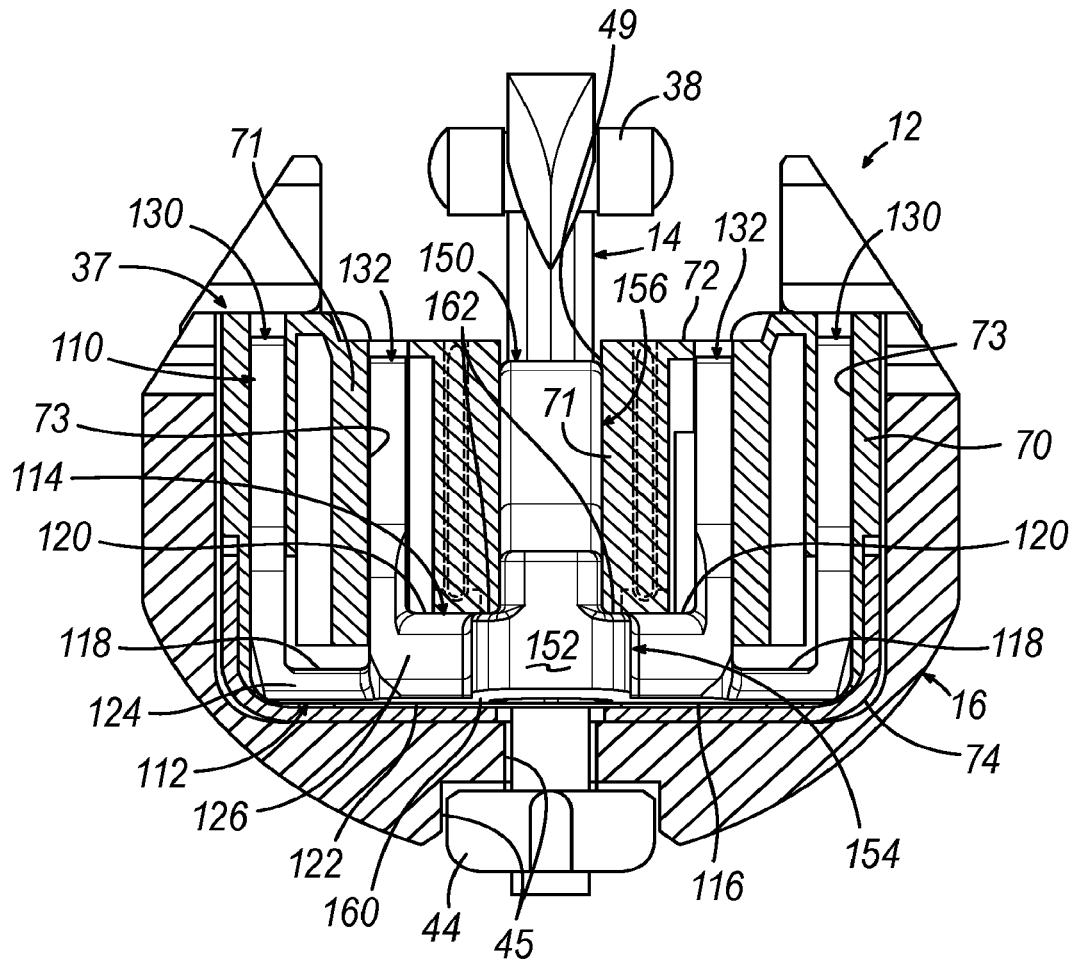
FIG. 10 depicts an end cross-sectional view of the end effector of FIG. 3 with the wedge sled of FIG. 8 captured between a cartridge body and a cartridge tray of a staple cartridge of the end effector.

In some instances, it may be desirable to provide a wedge sled that is configured to provide rigidity to staple cartridge (37) by supporting and/or stabilizing the walls of cartridge body (70) adjacent to the wedge sled to thereby promote alignment between staple apertures (51) and the corresponding staple forming pockets (53) during clamping of tissue between staple cartridge (37) and anvil (18) and/or during firing. In addition or alternatively, it may be desirable to provide a wedge sled having multiple distinct surface finishes (also referred to as "surface textures" or "surface topographies"). Such multiple distinct surface finishes may allow a wedge sled manufactured via a process which imparts an initial, relatively rough surface finish to the surfaces of the entire wedge sled to have select surfaces provided with a final, relatively smooth surface finish so that the select surfaces may smoothly interact with corresponding portions of staple cartridge (37), such as staple drivers (43). FIGS. 8-10 show an exemplary wedge sled (110) which provides such functionalities. Wedge sled (110) is similar to wedge sled (41) described above except as otherwise described below. For example, wedge sled (110) occupies the same amount of space longitudinally within staple cartridge (37) as wedge sled (41), making wedge sled (110) substantially interchangeable with wedge sled (41).

Wedge sled (110) of this example comprises a base including a base platform (112) and a central raised platform (114) extending upwardly from base platform (112). In the example shown, base platform (112) has a substantially flat bottom surface (116) defining a horizontal plane and configured to slide longitudinally along tray (74) while wedge sled (110) moves longitudinally through staple cartridge (37). Base platform (112) also has a laterally-opposed pair of substantially flat top surfaces (118) parallel to bottom surface (116), and raised platform (114) similarly has a laterally-opposed pair of substantially flat top surfaces (120) parallel to bottom surface (116). As best shown in FIG. 10, top surfaces (118, 120) are configured to confront and/or slidably contact or otherwise engage respective bottom surfaces of corresponding walls (71) of cartridge body (70) to thereby vertically support the corresponding walls (71) while wedge sled (110) moves longitudinally through staple cartridge (37).

The base of the present version also includes a lower chamfer (122) inclined upwardly and distally from a distal end of bottom surface (116) to outer and inner distal ends of base platform (112); a pair of outer upper chamfers (124) inclined downwardly and distally from respective distal ends of top surfaces (118) of base platform (112) to the outer distal ends of base platform (112); and a pair of inner upper chamfers (126) inclined downwardly and distally from respective distal ends of top surfaces (120) of raised platform (114) to the inner distal ends of base platform (112). Chamfers (122, 124, 126) may also be referred to as "tapered surfaces" or "bevels." Lower chamfer (122) may extend across a width of base platform (112) and may have a length greater than a thickness of base platform (112) (e.g., between bottom surface (116) and either top surface (118)). Likewise, outer upper chamfers (124) may each have a length greater than a thickness of base platform (112). Lower chamfer (122) may be configured to promote unimpeded longitudinal movement of wedge sled (110) through staple cartridge (37) in the distal direction by reducing the likelihood of the distal end of base platform (112) catching, or otherwise being obstructed by, tray (74). For example, lower chamfer (122) may urge tray (74) (which may be constructed of a flexible material) slightly downwardly away from the bottom surfaces of walls (71) of cartridge body (70) as wedge sled (110) is driven distally through staple cartridge (37). In some versions, any one or more of chamfers (122, 124, 126) may be omitted. For example, any one or more of chamfers (122, 124, 126) may be replaced by one or more respective fillets.

Wedge sled (110) further comprises a laterally-opposed pair of outer sled rails (130) extending upwardly from base platform (112), and a laterally-opposed pair of inner sled rails (132) extending upwardly from both base platform (112) and raised platform (114). Sled rails (130, 132) may also be referred to as "cam ramps" or "cam wedges." Sled rails (130, 132) of the present version extend substantially straight and upright from the respective top surfaces (118, 120) of base platform (112) and raised platform (114), such that sled rails (130, 132) are perpendicularly oriented relative to the horizontal plane and parallel to a vertical-longitudinal plane. In the example shown, inner sled rails (132) are laterally spaced apart from adjacent outer sled rails (130) to define top surfaces (118) of base platform (112). In this regard, top surfaces (118) of base platform (112) each extend at least partially along the lengths of sled rails (130, 132), and top surfaces (120) of raised platform (114) each extend at least partially along the length of the respective inner sled rail (132). Outer sled rails (130) of the present version each have a first height relative to bottom surface (116) of base platform (112), while inner sled rails (132) each have a second height relative to bottom surface (116) of base platform (112) that is less than the first height. Also in the example shown, outer and inner sled rails (130, 132) each terminate proximally at a same longitudinal position (e.g., at a proximal end of base platform (112)), while outer sled rails (130) each terminate distally at a first longitudinal position and inner sled rails (132) each terminate distally at a second longitudinal position that is distal relative to the first longitudinal position, such that outer sled rails (130) each have a first length and inner sled rails (132) each have a second length that is greater than the first length. Thus, the distal ends of outer sled rails (130) are aligned with each other in the longitudinal direction, and the distal ends of inner sled rails (132) are aligned with each other and offset from the distal ends of outer sled rails (130) in the longitudinal direction.

As best shown in FIG. 10, sled rails (130, 132) are configured to be received within corresponding longitudinally-extending slots (73) of cartridge body (70), and to slidably contact or otherwise engage respective side surfaces of corresponding walls (71) of cartridge body (70) to thereby horizontally stabilize walls (71) while wedge sled (110) moves longitudinally through staple cartridge (37). For example, outer and inner sled rails (130, 132) may inhibit laterally inward and/or laterally outward deflection (e.g., bending) of walls (71). In this regard, sled rails (130, 132) may each have a thickness equal to or slightly less than a width of the corresponding slot (73). In some versions, sled rails (130, 132) may additionally or alternatively be configured to slidably contact or otherwise engage respective upper slot surfaces of corresponding slots (73) of cartridge body (70) to thereby vertically support upper deck (72) while wedge sled (110) moves longitudinally through staple cartridge (37).

Each sled rail (130, 132) of wedge sled (110) presents one or more respective inclined cam surfaces (140, 142, 144, 146) for lifting staple drivers (43) upwardly as wedge sled (110) is driven distally through staple cartridge (37) to drive the corresponding staples (47) out through the corresponding staple apertures (51). In the example shown, each outer sled rail (130) includes a leading cam surface (140) oriented at a first angle relative to the horizontal plane defined by bottom surface (116) and a trailing cam surface (142) oriented at a second angle relative to the horizontal plane, such that outer sled rails (130) have a same side elevational profile as each other. Likewise, each inner sled rail (132) includes a leading cam surface (144) oriented at the first angle relative to the horizontal plane and a trailing cam surface (146) oriented at a third angle relative to the horizontal plane, such that inner sled rails (132) have a same side elevational profile as each other and a different elevational profile from that of outer sled rails (130). Thus, wedge sled (110) may be substantially symmetric about the vertical-longitudinal plane, at least with respect to the configurations of sled rails (130, 132).

In the present version, the first angle is greater than the second angle, which is greater than the third angle. Alternatively, any other suitable relative angles may be used. In the example shown, upper chamfers (124, 126) are also oriented at the first angle relative to the horizontal plane such that each leading cam surface (140) of outer sled rails (130) is seamlessly contiguous with the respective outer upper chamfer (124) (and has an overlapping side elevational profile therewith) to collectively define a single continuous surface, and such that each leading cam surface (144) of inner sled rails (132) is seamlessly contiguous with the respective inner upper chamfer (126) (and has an overlapping side elevational profile therewith) to collectively define another single continuous surface.

Wedge sled (110) further comprises a central nose (150) extending upwardly from raised platform (114) between inner sled rails (132) and also extending distally from both raised platform (114) and base platform (112) to a distal tip (152). In the example shown, central nose (150) is laterally spaced apart from each inner sled rail (132) to define top surfaces (120) of raised platform (114). More particularly, central nose (150) is equally spaced apart from inner sled rails (132). Central nose (150) of the present version includes a lower portion (154) extending distally from both base platform (112) and raised platform (114) to distal tip (152), and an upper portion (156) extending upwardly from both raised platform (114) and lower portion (154).

As best shown in FIG. 9, lower portion (154) of central nose (150) of the present version includes a tapered bottom surface (160) inclined downwardly and proximally from distal tip to lower chamfer (122) of base platform (112). Tapered bottom surface (160) may be configured to promote unimpeded longitudinal movement of wedge sled (110) through staple cartridge (37) in the distal direction by reducing the likelihood of distal tip (152) catching, or otherwise being obstructed by, tray (74). For example, tapered bottom surface (160) may urge tray (74) (which may be constructed of a flexible material) slightly downwardly away from the bottom surfaces of walls (71) of cartridge body (70) as wedge sled (110) is driven distally through staple cartridge (37). In the example shown, tapered bottom surface (160) is oriented at a same angle relative to the horizontal plane defined by bottom surface (116) as lower chamfer (122) such that tapered bottom surface (160) is seamlessly contiguous with lower chamfer (122) to collectively define a single continuous chamfer for further promoting unimpeded longitudinal movement of wedge sled (110) through staple cartridge (37) in the distal direction. In some versions, tapered bottom surface (160) may be omitted. For example, tapered bottom surface (160) may be replaced by one or more respective fillets.

Upper portion (156) of central nose (150) of the present version is substantially perpendicular to the horizontal plane defined by bottom surface (116). As shown, upper portion (156) extends longitudinally from a proximal end of raised platform (114) to distal tip (152), such that upper portion (156) is at least partially positioned distally relative to a distal end of base platform (112) and relative to distal ends of sled rails (130, 132), and such that upper portion (156) extends at least partially along the length of each sled rail (130, 132).

In the example shown, lower portion (154) of central nose (150) extends laterally outwardly relative to upper portion (156) on opposing sides of upper portion (156) to define a laterally-opposed pair of upwardly-facing ledge surfaces (162) extending longitudinally from respective top surfaces (120) of raised platform (114) to distal tip (152). More particularly, ledge surfaces (162) are substantially flat, parallel to the horizontal plane defined by bottom surface (116), and positioned at a same height as top surfaces (120) of raised platform (114) relative to bottom surface (116), such that ledge surfaces (162) are seamlessly contiguous with respective top surfaces (120) of raised platform (114) to collectively define respective single continuous surfaces. As shown, each ledge surface (162) is at least partially positioned distally relative to a distal end of base platform (112) and relative to distal ends of sled rails (130, 132).

As best shown in FIG. 10, central nose (150) is configured to be at least partially received within vertical slot (49) of staple cartridge (37). In some versions, central nose (150) is configured to slidably contact or otherwise engage inner walls (71) of cartridge body (70) to thereby vertically support and/or horizontally stabilize inner walls (71) while wedge sled (110) moves longitudinally through staple cartridge (37). In this regard, ledge surfaces (162) of the present version confront and slidably contact or otherwise engage respective lower surfaces of inner walls (71) to thereby vertically support inner walls (71) while wedge sled (110) moves longitudinally through staple cartridge (37). In addition, upper portion (156) of the present version slidably contacts or otherwise engages laterally inward surfaces of inner walls (71) to thereby horizontally stabilize inner walls (71) while wedge sled (110) moves longitudinally through staple cartridge (37). For example, upper portion (156) may inhibit laterally inward deflection (e.g., bending) of inner walls (71). In this regard, upper portion (156) may have a thickness equal to or slightly less than a width of vertical slot (49), while lower portion (154) may have a thickness greater than the width of vertical slot (49).

Since each ledge surface (162) of central nose (150) is at least partially positioned distally relative to distal ends of sled rails (130, 132), ledge surfaces (162) may vertically support inner walls (71) of cartridge body (70) at longitudinal positions that are distal relative to sled rails (130, 132) while wedge sled (110) moves longitudinally through staple cartridge (37). Likewise, since upper portion (156) is at least partially positioned distally relative to distal ends of sled rails (130, 132), upper portion (156) may horizontally stabilize inner walls (71) of cartridge body (70) at longitudinal positions that are distal relative to sled rails (130, 132) while wedge sled (110) moves longitudinally through staple cartridge (37). In this manner, central nose (150) may provide vertical support and/or horizontal stability to cartridge body (70) at longitudinal positions corresponding to each staple aperture (51) along the length of cartridge body (70) in advance of (e.g., at least immediately prior to) the corresponding sled rail (130, 132) lifting the corresponding staple driver (43) to drive the corresponding staple (47) out through staple aperture (51). By providing vertical support and/or horizontal stability to cartridge body (70) at such longitudinal positions in advance of lifting staple drivers (43) to drive staples (47) out through staple apertures (51) at such longitudinal positions, central nose (150) may promote proper alignment of each staple aperture (51) with the corresponding staple forming pocket (53) on the inner surface of anvil (18) in advance of deploying and forming each staple (47). For example, central nose (150) may promote vertical and/or angular alignment of each staple aperture (51) with the corresponding staple forming pocket (53) by assisting in maintaining upper deck (72) substantially parallel to the inner surface of anvil (18) having staple forming pockets (53), and/or by inhibiting lateral deflection of inner walls (71) which might otherwise cause staple apertures (51) to be angled (e.g., laterally inwardly or laterally outwardly) relative to the corresponding staple forming pocket (53).

Moreover, since top surfaces (118, 120) of base platform (112) and raised platform (114) each extend at least partially along the length of the respective sled rail (130, 132), top surfaces (118, 120) may vertically support corresponding walls (71) of cartridge body (70) at the same longitudinal positions at which sled rails (130, 132) are located while wedge sled (110) moves longitudinally through staple cartridge (37). In this manner, base platform (112) and/or raised platform (114) may provide vertical support to cartridge body (70) at longitudinal positions corresponding to each staple aperture (51) along the length of cartridge body (70) substantially contemporaneously with (e.g., during at least a portion of the duration of) the corresponding sled rail (130, 132) lifting the corresponding staple driver (43) to drive the corresponding staple (47) out through staple aperture (51). By providing vertical support to cartridge body (70) at such longitudinal positions substantially contemporaneously with lifting staple drivers (43) to drive staples (47) out through staple apertures (51) at such longitudinal positions, base platform (112) and/or raised platform (114) may promote proper alignment of each staple aperture (51) with the corresponding staple forming pocket (53) on the inner surface of anvil (18) while deploying and forming each staple (47). For example, base platform (112) and/or raised platform (114) may promote vertical and/or angular alignment of each staple aperture (51) with the corresponding staple forming pocket (53) by assisting in maintaining upper deck (72) substantially parallel to the inner surface of anvil (18) having staple forming pockets (53). Since top surfaces (120) of raised platform (114) are seamlessly contiguous with respective ledge surfaces (162), central nose (150) and raised platform (114) may cooperatively promote continuous proper alignment of each staple aperture (51) with the corresponding staple forming pocket (53) on the inner surface of anvil (18) from at least immediately prior to deploying and forming each staple (47) to completion of deploying and forming each staple (47).

Additionally, since upper portion (156) of central nose (150) extends at least partially along the length of each sled rail (130, 132), upper portion (156) may horizontally stabilize inner walls (71) of cartridge body (70) at the same longitudinal positions at which sled rails (130, 132) are located while wedge sled (110) moves longitudinally through staple cartridge (37). In this manner, central nose (150) may provide horizontal stability to cartridge body (70) at longitudinal positions corresponding to each staple aperture (51) along the length of cartridge body (70) substantially contemporaneously with (e.g., during at least a portion of the duration of) the corresponding sled rail (130, 132) lifting the corresponding staple driver (43) to drive the corresponding staple (47) out through staple aperture (51). By providing horizontal stability to cartridge body (70) at such longitudinal positions substantially contemporaneously with lifting staple drivers (43) to drive staples (47) out through staple apertures (51) at such longitudinal positions, central nose (150) may promote proper alignment of each staple aperture (51) with the corresponding staple forming pocket (53) on the inner surface of anvil (18) while deploying and forming each staple (47). For example, central nose (150) may promote vertical and/or angular alignment of each staple aperture (51) with the corresponding staple forming pocket (53) by inhibiting lateral deflection of inner walls (71) which might otherwise cause staple apertures (51) to be angled (e.g., laterally inwardly or laterally outwardly) relative to the corresponding staple forming pocket (53). As discussed above, sled rails (130, 132) may themselves horizontally stabilize corresponding walls (71) of cartridge body (70) at their respective longitudinal positions, and thus may also promote vertical and/or angular alignment of each staple aperture (51) with the corresponding staple forming pocket (53) by inhibiting lateral deflection of inner walls (71) which might otherwise cause staple apertures (51) to be angled (e.g., laterally inwardly or laterally outwardly) relative to the corresponding staple forming pocket (53). Therefore, central nose (150) and sled rails (130, 132) may cooperatively provide horizontal stability to cartridge body (70) at the respective longitudinal positions of each sled rail (130, 132) while wedge sled (110) moves longitudinally through staple cartridge (37). It should be understood that anvil (18) is intentionally omitted from the view in FIG. 10.

Wedge sled (110) may be formed of any suitable material or combination of materials, including but not limited to metallic materials such as stainless steel (e.g., hardened stainless steel) or titanium. In some versions, wedge sled (110) may be manufactured via a metal injection molding (MIM) process. It will be appreciated that such a MIM process may provide wedge sled (110) with improved compression support and reduced lateral deflection, and may enable wedge sled (110) to provide improved vertical support and/or horizontal stability to cartridge body (70) during use (e.g., clamping and/or firing), as compared to a wedge sled (110) formed of a plastic material, for example. Such a MIM process may include molding wedge sled (110) as a single unitary piece from a liquid MIM feedstock mix of metal powder and binder, for example. The MIM process may further include subjecting wedge sled (110) to various types of conditioning, including but not limited to cleaning, thermal debinding, and/or sintering.

In any event, after the MIM process is complete, all surfaces of wedge sled (110) may have an initial (e.g., raw MIM) surface finish, including cam surfaces (140, 142, 144, 146) of sled rails (130, 132). Such an initial surface finish may be rough, abrasive, and/or granular, and may generally be similar to the texture of pitted sandpaper. Thus, select surfaces of wedge sled (110) may be further conditioned to refine or otherwise remove the initial surface finish from the select surfaces and provide the select surfaces with a final surface finish that is relatively smoother (e.g., finer, more polished) than the initial surface finish. For example, cam surfaces (140, 142, 144, 146) of sled rails (130, 132) may be machined to remove the initial surface finish from cam surfaces (140, 142, 144, 146) and provide cam surfaces (140, 142, 144, 146) with such a final surface finish. The final surface finish of cam surfaces (140, 142, 144, 146) may promote reduced friction and smooth interaction between cam surfaces (140, 142, 144, 146) and staple drivers (43) and thereby minimize wearing of the portions of staple drivers (43) contacted by cam surfaces (140, 142, 144, 146).

While the select surfaces provided with the final surface finish have been described in the form of cam surfaces (140, 142, 144, 146), it will be appreciated that any other surfaces of wedge sled (110) may additionally or alternatively be provided with the final surface finish. For example, bottom surface (116) may be provided with the final surface finish to promote reduced friction and smooth interaction between bottom surface (116) and tray (74).

In some versions, the remaining, non-select surfaces of wedge sled (110) may not be further conditioned such that the initial surface finish may remain on the non-select surfaces during use (e.g., clamping and/or firing). For example, top surfaces (118, 120) of base platform (112) and raised platform (114) and/or ledge surfaces (162) of central nose (150) may retain the initial surface finish. As another example, every surface of wedge sled (110) other than cam surfaces (140, 142, 144, 146) of sled rails (130, 132) may retain the initial surface finish. Thus, the select surfaces of wedge sled (110) may have the final surface finish while the non-select surfaces of wedge sled (110) may have the initial surface finish, such that wedge sled (110) may have at least two distinct surface finishes.

The select and non-select surfaces may be determined based on the particular components of staple cartridge (37) and/or firing beam (14) with which each individual surface of wedge sled (110) interacts. In this regard, the final surface finish may be more desirable for surfaces of wedge sled (110) which interact with certain predetermined components of staple cartridge (37) and/or firing beam (14) than others. For example, cam surfaces (140, 142, 144, 146) of sled rails (130, 132) may be selected to receive the final surface finish based on their interaction with staple drivers (43), while the remaining surfaces of sled rails (130, 132), top surfaces (118) of base platform (112), top surfaces (120) of raised platform (114), and/or ledge surfaces (162) of central nose (150) may not be selected to receive the final surface finish based on their interaction with cartridge body (70). As another example, bottom surface (116) may be selected to receive the final surface finish based on its interaction with tray (74), while a proximal end surface of wedge sled (110)

may not be selected to receive the final surface finish based on its interaction with pusher block (80).

III. EXEMPLARY SLED HAVING CARTRIDGE WALL SUPPORT FEATURE, STAPLE DRIVER SUPPORT FEATURE, TAPERED DISTAL END, AND MULTIPLE SURFACE FINISHES

Figure 11:
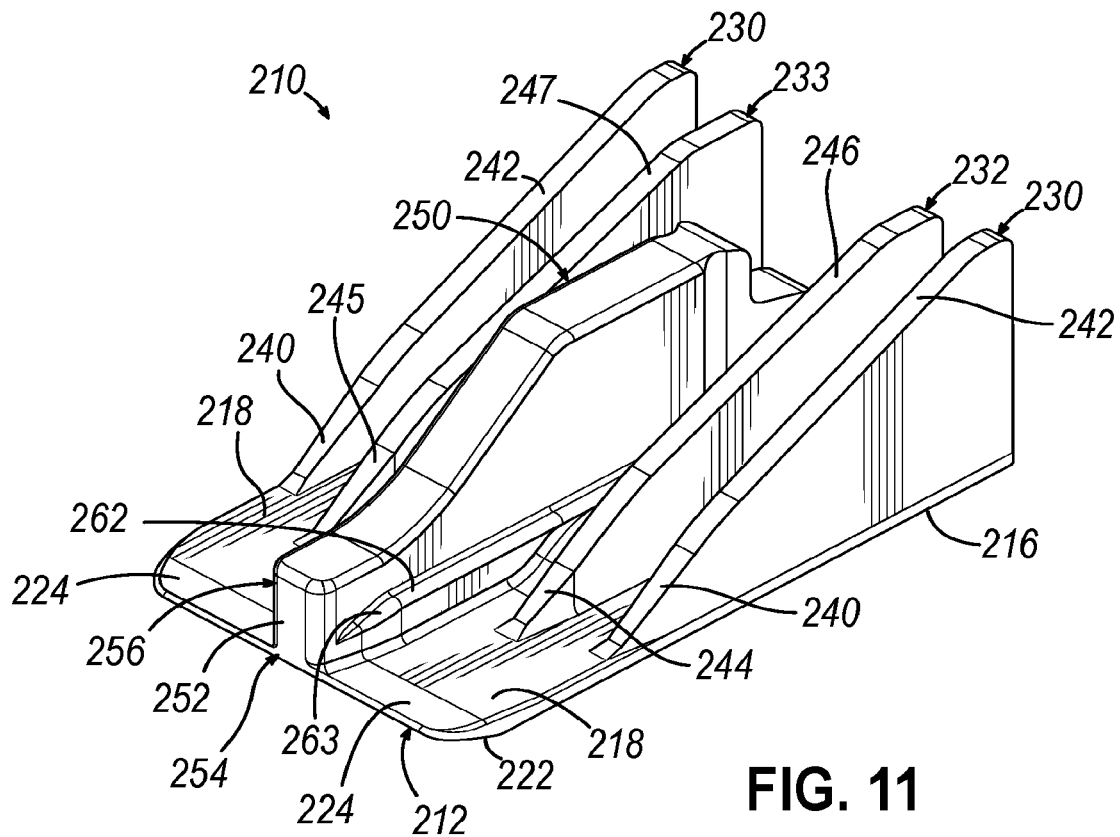
FIG. 11 depicts a perspective view of another example of a wedge sled for actuating the staple drivers of the instrument of FIG. 1, showing the wedge sled having a cartridge wall support feature, a staple driver support feature, a tapered distal end, and multiple surface finishes.
Figure 12:
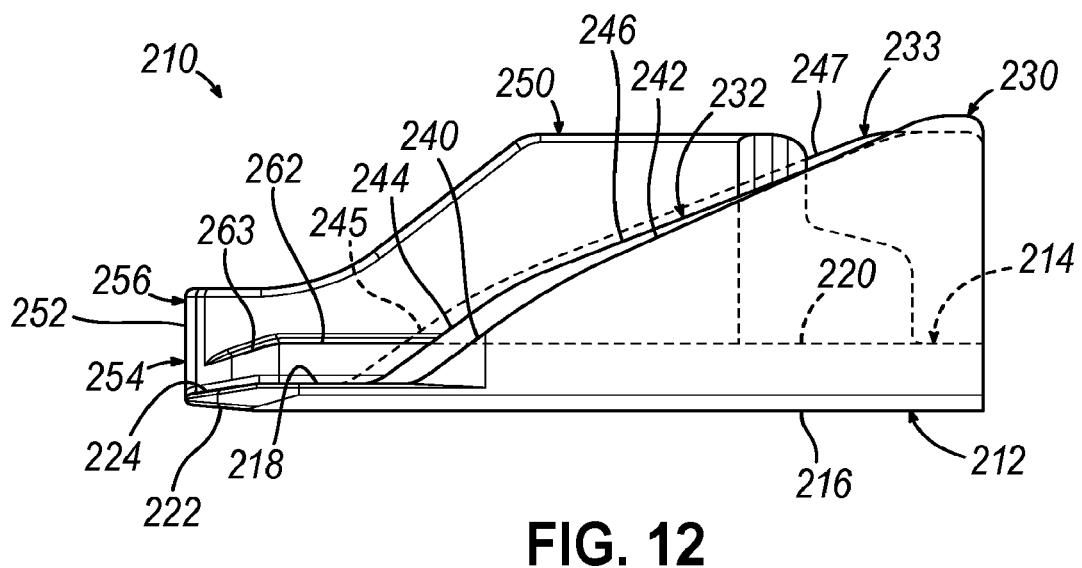
FIG. 12 depicts a side view of the wedge sled of FIG. 11.
Figure 13:
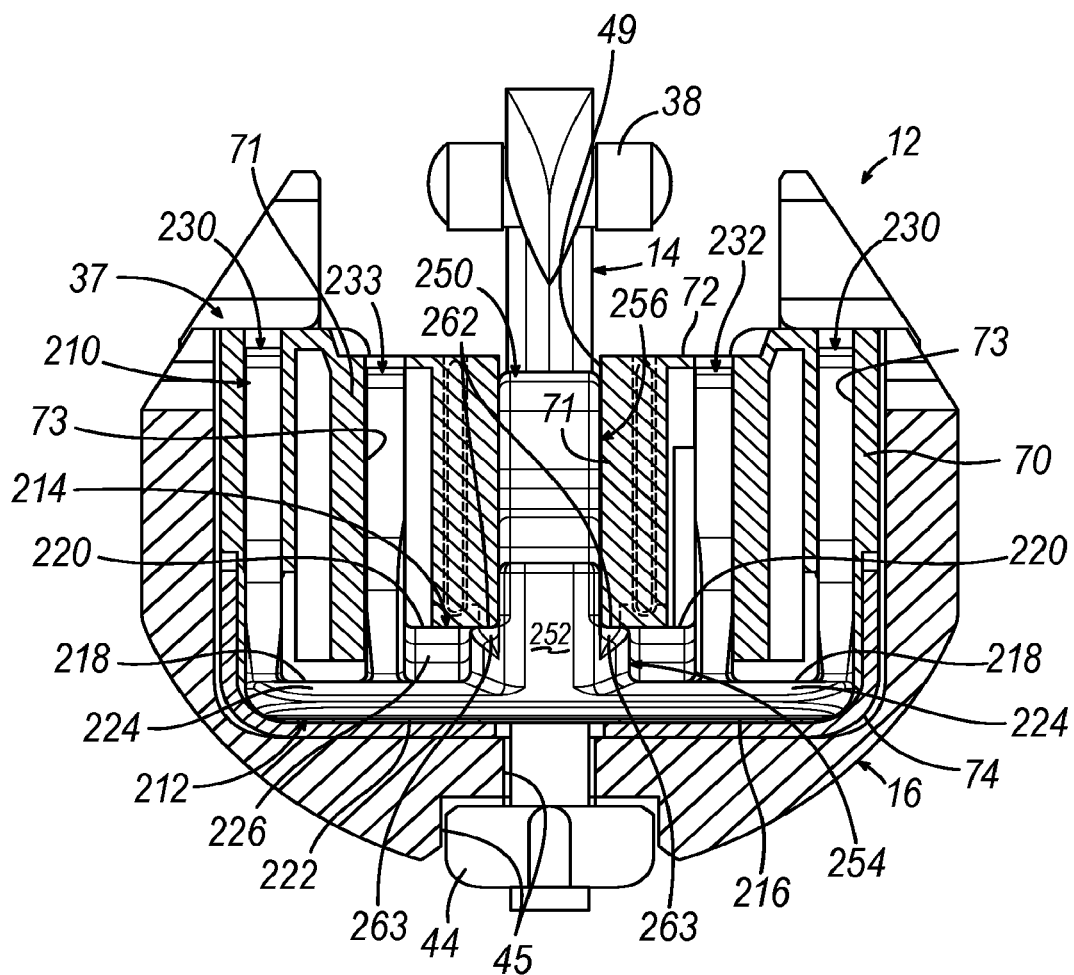
FIG. 13 depicts an end cross-sectional view of the end effector of FIG. 3 with the wedge sled of FIG. 11 captured between the cartridge body and the cartridge tray of the staple cartridge of the end effector.

In some instances, it may be desirable to provide a wedge sled that is configured to support staple drivers (43) prior to fully lifting staple drivers (43) to drive the corresponding staples (47) out through the corresponding staple apertures (51), to thereby promote alignment between staple drivers (43) and the corresponding staple forming pockets (53) during firing. In addition or alternatively, it may be desirable to provide a wedge sled that is configured to provide rigidity to staple cartridge (37) and/or that has multiple distinct surface finishes (also referred to as "surface textures" or "surface topographies") as discussed above with respect to wedge sled (110). FIGS. 11-13 show an exemplary wedge sled (210) which provides such functionalities. Wedge sled (210) is similar to wedge sled (110) described above except as otherwise described below. For example, wedge sled (210) occupies the same amount of space longitudinally within staple cartridge (37) as wedge sleds (41, 110), making wedge sled (210) substantially interchangeable with wedge sleds (41, 110).

Wedge sled (210) of this example comprises a base including a base platform (212) and a central raised platform (214) extending upwardly from base platform (212). In the example shown, base platform (212) has a substantially flat bottom surface (216) defining a horizontal plane and configured to slide longitudinally along tray (74) while wedge sled (210) moves longitudinally through staple cartridge (37). Base platform (212) also has a laterally-opposed pair of substantially flat top surfaces (218) parallel to bottom surface (216), and raised platform (214) similarly has a laterally-opposed pair of substantially flat top surfaces (220) parallel to bottom surface (216). As best shown in FIG. 13, top surfaces (218, 220) are configured to confront and/or slidably contact or otherwise engage respective bottom surfaces of corresponding walls (71) of cartridge body (70) to thereby vertically support the corresponding walls (71) while wedge sled (210) moves longitudinally through staple cartridge (37). In the present example, top surfaces (218) of base platform (212) are further configured to slidably contact or otherwise engage respective staple drivers (43) to thereby vertically support the respective staple drivers (43) while wedge sled (210) moves longitudinally through staple cartridge (37), as described in greater detail below.

The base of the present version also includes a lower chamfer (222) inclined upwardly and distally from a distal end of bottom surface (216) to a distal end of base platform (212); a pair of distal upper chamfers (224) inclined downwardly and distally from respective distal ends of top surfaces (218) of base platform (212) to the distal end of base platform (212); and a pair of proximal upper chamfers (226) inclined downwardly and distally from respective distal ends of top surfaces (220) of raised platform (214) to respective top surfaces (218) of base platform. Chamfers (222, 224, 226) may also be referred to as "tapered surfaces" or "bevels." Lower chamfer (222) may extend across a width of base platform (212) and may have a length greater than a thickness of base platform (212) (e.g., between bottom surface (216) and either top surface (218)). Likewise, distal upper chamfers (224) may each have a length greater than a thickness of base platform (212). Lower chamfer (222) may be configured to promote unimpeded longitudinal movement of wedge sled (210) through staple cartridge (37) in the distal direction by reducing the likelihood of the distal end of base platform (212) catching, or otherwise being obstructed by, tray (74). For example, lower chamfer (222) may urge tray (74) (which may be constructed of a flexible material) slightly downwardly away from the bottom surfaces of walls (71) of cartridge body (70) as wedge sled (210) is driven distally through staple cartridge (37). Distal upper chamfers (224) may be configured to partially lift staple drivers (43) upwardly onto respective top surfaces (218) of base platform (212) without driving the corresponding staples (47) out through the corresponding staple apertures (51) as wedge sled (210) is driven distally through staple cartridge (37). For example, distal upper chamfers (224) may be configured to cammingly engage staple drivers (43) to urge staple drivers (43) onto respective top surfaces (218). In addition or alternatively, distal upper chamfers (224) may be configured to lift outer walls (71) of cartridge body (70) slightly upwardly onto respective top surfaces (218) of base platform (212) as wedge sled (210) is driven distally through staple cartridge (37). For example, distal upper chamfers (224) may be configured to cammingly engage outer walls (71) to urge outer walls (71) onto respective top surfaces (218), as described in greater detail below. In some versions, any one or more of chamfers (222, 224, 226) may be omitted. For example, any one or more of chamfers (222, 224, 226) may be replaced by one or more respective fillets.

Wedge sled (210) further comprises a laterally-opposed pair of outer sled rails (230) extending upwardly from base platform (212), and laterally-opposed first and second inner sled rails (232, 233) extending upwardly from both base platform (212) and raised platform (214). Sled rails (230, 232, 233) may also be referred to as "cam ramps" or "cam wedges." Sled rails (230, 232, 233) of the present version extend substantially straight and upright from the respective top surfaces (218, 220) of base platform (212) and raised platform (214), such that sled rails (230, 232, 233) are perpendicularly oriented relative to the horizontal plane and parallel to a vertical-longitudinal plane. In the example shown, inner sled rails (232, 233) are laterally spaced apart from adjacent outer sled rails (230) to define top surfaces (218) of base platform (212). In this regard, top surfaces (218) of base platform (212) each extend at least partially along the lengths of sled rails (230, 232, 233), and top surfaces (220) of raised platform (214) each extend at least partially along the length of the respective inner sled rail (232, 233). Moreover, top surfaces (218) of base platform (212) are each at least partially positioned distally relative to distal ends of sled rails (230, 232, 233). Outer sled rails (230) of the present version each have a first height relative to bottom surface (216) of base platform (212), while inner sled rails (232, 233) each have a second height relative to bottom surface (216) of base platform (212) that is less than the first height. Also in the example shown, outer and inner sled rails (230, 232, 233) each terminate proximally at a same longitudinal position (e.g., at a proximal end of base platform (212)), while outer sled rails (230) each terminate distally at a first longitudinal position, first inner sled rail (232) terminates distally at a second longitudinal position that is distal relative to the first longitudinal position, and second inner sled rail (233) terminates distally at a third longitudinal position that is distal relative to the first and second longitudinal positions, such that outer sled rails (230) each have a first length, first inner sled rail (232) has a second length that is greater than the first length, and second inner sled rail (233) has a third length that is greater than the first and second lengths. Thus, the distal ends of outer sled rails (230) are aligned with each other in the longitudinal direction, and the distal ends of first and second inner sled rails (232, 233) are offset from each other and from the distal ends of outer sled rails (230) in the longitudinal direction.

Each sled rail (230, 232, 233) is longitudinally aligned with a respective distal upper chamfer (224) of the base such that a respective top surface (218) of base platform (212) extends longitudinally between each sled rail (230, 232, 233) and the respective distal upper chamfer (224). In some versions, the distal ends of sled rails (230, 232, 233) may each be spaced apart from the respective distal upper chamfers (224) by a distance equal to or greater than a length of the corresponding staple drivers (43) such that the respective top surface (218) may be capable of supporting the corresponding staple drivers (43) between each sled rail (230, 232, 233) and respective distal upper chamfer (224) in an upright manner.

As best shown in FIG. 13, sled rails (230, 232, 233) are configured to be received within corresponding longitudinally-extending slots (73) of cartridge body (70), and to slidably contact or otherwise engage respective side surfaces of corresponding walls (71) of cartridge body (70) to thereby horizontally stabilize walls (71) while wedge sled (210) moves longitudinally through staple cartridge (37). For example, outer and inner sled rails (230, 232, 233) may inhibit laterally inward and/or laterally outward deflection (e.g., bending) of walls (71). In this regard, sled rails (230, 232, 233) may each have a thickness equal to or slightly less than a width of the corresponding slot (73). In some versions, sled rails (230, 232, 233) may additionally or alternatively be configured to slidably contact or otherwise engage respective upper slot surfaces of corresponding slots (73) of cartridge body (70) to thereby vertically support upper deck (72) while wedge sled (210) moves longitudinally through staple cartridge (37).

Each sled rail (230, 232, 233) of wedge sled (210) presents one or more respective inclined cam surfaces (240, 242, 244, 245, 246, 247) for fully lifting staple drivers (43) upwardly as wedge sled (210) is driven distally through staple cartridge (37) to drive the corresponding staples (47) out through the corresponding staple apertures (51). In the example shown, each outer sled rail (230) includes a leading cam surface (240) oriented at a first angle relative to the horizontal plane defined by bottom surface (216) and a trailing cam surface (242) oriented at a second angle relative to the horizontal plane, such that outer sled rails (230) have a same side elevational profile as each other. Likewise, first and second inner sled rails (232, 233) each include a leading cam surface (244, 245) oriented at the first angle relative to the horizontal plane. In the example shown, first inner sled rail (232) includes a trailing cam surface (246) oriented at a third angle relative to the horizontal plane and second inner sled rail (233) includes a trailing cam surface (247) oriented at a fourth angle relative to the horizontal plane, such that inner sled rails (232, 233) have different elevational profiles from each other and from that of outer sled rails (230). Thus, wedge sled (210) may be substantially asymmetric about the vertical-longitudinal plane, at least with respect to the configurations of sled rails (230, 232, 233).

In the present version, the first angle is greater than the second angle, which is greater than the third angle, which is greater than the fourth angle. Alternatively, any other suitable relative angles may be used.

Wedge sled (210) further comprises a central nose (250) extending upwardly from both base platform (212) and raised platform (214) between inner sled rails (232, 233) and also extending distally from raised platform (214) to a distal tip (252). In the example shown, central nose (250) is laterally spaced apart from each inner sled rail (232, 233) to define top surfaces (220) of raised platform (214). More particularly, central nose (250) is equally spaced apart from inner sled rails (232, 233). Central nose (250) of the present version includes a lower portion (254) extending distally from raised platform (214) to distal tip (252), and an upper portion (256) extending upwardly from both raised platform (214) and lower portion (254). Upper portion (256) of the present version is substantially perpendicular to the horizontal plane. As shown, upper portion (256) extends longitudinally from a proximal end of raised platform (214) to distal tip (252), such that upper portion (256) is at least partially positioned distally relative to distal ends of sled rails (230, 232, 233), and such that upper portion (256) extends at least partially along the length of each sled rail (230, 232, 233). Distal tip (252) of the present version is positioned at a same longitudinal position as the distal end of base platform (212).

In the example shown, lower portion (254) extends laterally outwardly relative to upper portion (256) on opposing sides of upper portion (256) to define a laterally-opposed pair of upwardly-facing ledge surfaces (262) extending longitudinally from respective top surfaces (220) of raised platform (214) toward distal tip (252). More particularly, ledge surfaces (262) are substantially flat, parallel to the horizontal plane, and positioned at a same height as top surfaces (220) of raised platform (214) relative to bottom surface (216), such that ledge surfaces (262) are seamlessly contiguous with respective top surfaces (220) of raised platform (214) to collectively define respective single continuous surfaces. As shown, each ledge surface (262) is at least partially positioned distally relative to distal ends of sled rails (230, 232, 233). Central nose (250) of the present version further includes a laterally-opposed pair of distal tapered surfaces (263) inclined downwardly and distally from respective distal ends of ledge surfaces (262) toward distal tip (252) to thereby include an upwardly facing distal surface and to define a distal-most end coming to a distal-most point (also referred to as a point). Tapered surfaces (263) may be configured to lift inner walls (71) of cartridge body (70) slightly upwardly onto respective ledge surfaces (262) of central nose (250) as wedge sled (210) is driven distally through staple cartridge (37). For example, tapered surfaces (263) may be configured to cammingly engage inner walls (71) to urge inner walls (71) onto respective ledge surfaces (262), as described in greater detail below. In some versions, any one or more of tapered surfaces (263) may be omitted. For example, any one or more of tapered surfaces (263) may be replaced by one or more respective fillets.

As best shown in FIG. 13, central nose (250) is configured to be at least partially received within vertical slot (49) of staple cartridge (37). In some versions, central nose (250) is configured to slidably contact or otherwise engage inner walls (71) of cartridge body (70) to thereby vertically support and/or horizontally stabilize inner walls (71) while wedge sled (210) moves longitudinally through staple cartridge (37). In this regard, ledge surfaces (262) of the present version confront and slidably contact or otherwise engage respective lower surfaces of inner walls (71) to thereby vertically support inner walls (71) while wedge sled (210) moves longitudinally through staple cartridge (37). In addition, upper portion (256) of the present version contacts or otherwise engages laterally inward surfaces of inner walls

(71) to thereby horizontally stabilize inner walls (71) while wedge sled (210) moves longitudinally through staple cartridge (37). For example, upper portion (256) may inhibit laterally inward deflection (e.g., bending) of inner walls (71). In this regard, upper portion (256) may have a thickness equal to or slightly less than a width of vertical slot (49), while lower portion (254) may have a thickness greater than the width of vertical slot (49).

Since each top surface (218) of base platform (212) is at least partially positioned distally relative to distal ends of sled rails (230, 232, 233), top surfaces (218) may vertically support staple drivers (43) and/or outer walls (71) of cartridge body (70) at longitudinal positions that are distal relative to sled rails (230, 232, 233) while wedge sled (210) moves longitudinally through staple cartridge (37). In this manner, base platform (212) may provide vertical support to staple drivers (43) and/or cartridge body (70) at longitudinal positions corresponding to each staple aperture (51) along the length of cartridge body (70) in advance of (e.g., at least immediately prior to) the corresponding sled rail (230, 232, 233) fully lifting the corresponding staple driver (43) to drive the corresponding staple (47) out through staple aperture (51). By providing vertical support to cartridge body (70) at such longitudinal positions in advance of fully lifting staple drivers (43) to drive staples (47) out through staple apertures (51) at such longitudinal positions, base platform (212) may promote proper alignment of each staple aperture (51) with the corresponding staple forming pocket (53) on the inner surface of anvil (18) in advance of deploying and forming each staple (47). For example, base platform (212) may promote vertical and/or angular alignment of each staple aperture (51) with the corresponding staple forming pocket (53) by assisting in maintaining upper deck (72) substantially parallel to the inner surface of anvil (18) having staple forming pockets (53). Likewise, by providing vertical support to staple drivers (43) at such longitudinal positions in advance of fully lifting staple drivers (43) to drive staples (47) out through staple apertures (51) at such longitudinal positions, base platform (212) may promote proper alignment of each staple driver (43) with the corresponding staple forming pocket (53) on the inner surface of anvil (18) in advance of deploying and forming each staple (47). For example, base platform (212) may promote vertical and/or angular alignment of each staple driver (43) with the corresponding staple forming pocket (53) by assisting in maintaining each staple driver (43) substantially perpendicularly oriented relative to the inner surface of anvil (18) having staple forming pockets (53), such as by inhibiting distal tipping of staple drivers (43) which might otherwise occur when leading cam surfaces (240, 244, 245) of sled rails (230, 232, 233) cammingly engage staple drivers (43).

Similarly, since each ledge surface (262) of central nose (250) is at least partially positioned distally relative to distal ends of sled rails (230, 232, 233), ledge surfaces (262) may vertically support inner walls (71) of cartridge body (70) at longitudinal positions that are distal relative to sled rails (230, 232, 233) while wedge sled (210) moves longitudinally through staple cartridge (37). Likewise, since upper portion (256) is at least partially positioned distally relative to distal ends of sled rails (230, 232, 233), upper portion (256) may horizontally stabilize inner walls (71) of cartridge body (70) at longitudinal positions that are distal relative to sled rails (230, 232, 233) while wedge sled (210) moves longitudinally through staple cartridge (37). In this manner, central nose (250) may provide vertical support and/or horizontal stability to cartridge body (70) at longitudinal positions corresponding to each staple aperture (51) along the length of cartridge body (70) in advance of (e.g., at least immediately prior to) the corresponding sled rail (230, 232, 233) fully lifting the corresponding staple driver (43) to drive the corresponding staple (47) out through staple aperture (51). By providing vertical support and/or horizontal stability to cartridge body (70) at such longitudinal positions in advance of fully lifting staple drivers (43) to drive staples (47) out through staple apertures (51) at such longitudinal positions, central nose (250) may promote proper alignment of each staple aperture (51) with the corresponding staple forming pocket (53) on the inner surface of anvil (18) in advance of deploying and forming each staple (47). For example, central nose (250) may promote vertical and/or angular alignment of each staple aperture (51) with the corresponding staple forming pocket (53) by assisting in maintaining upper deck (72) substantially parallel to the inner surface of anvil (18) having staple forming pockets (53), and/or by inhibiting lateral deflection of inner walls (71) which might otherwise cause staple apertures (51) to be angled (e.g., laterally inwardly or laterally outwardly) relative to the corresponding staple forming pocket (53).

Moreover, since top surfaces (218, 220) of base platform (212) and raised platform (214) each extend at least partially along the length of the respective sled rail (230, 232, 233), top surfaces (218, 220) may vertically support corresponding walls (71) of cartridge body (70) at the same longitudinal positions at which sled rails (230, 232, 233) are located while wedge sled (210) moves longitudinally through staple cartridge (37). In this manner, base platform (212) and/or raised platform (214) may provide vertical support to cartridge body (70) at longitudinal positions corresponding to each staple aperture (51) along the length of cartridge body (70) substantially contemporaneously with (e.g., during at least a portion of the duration of) the corresponding sled rail (230, 232, 233) fully lifting the corresponding staple driver (43) to drive the corresponding staple (47) out through staple aperture (51). By providing vertical support to cartridge body (70) at such longitudinal positions substantially contemporaneously with fully lifting staple drivers (43) to drive staples (47) out through staple apertures (51) at such longitudinal positions, base platform (212) and/or raised platform (214) may promote proper alignment of each staple aperture (51) with the corresponding staple forming pocket (53) on the inner surface of anvil (18) while deploying and forming each staple (47). For example, base platform (212) and/or raised platform (214) may promote vertical and/or angular alignment of each staple aperture (51) with the corresponding staple forming pocket (53) by assisting in maintaining upper deck (72) substantially parallel to the inner surface of anvil (18) having staple forming pockets (53). Since top surfaces (220) of raised platform (214) are seamlessly contiguous with respective ledge surfaces (262), central nose (250) and raised platform (214) may cooperatively promote continuous proper alignment of each staple aperture (51) with the corresponding staple forming pocket (53) on the inner surface of anvil (18) from at least immediately prior to deploying and forming each staple (47) to completion of deploying and forming each staple (47).

Additionally, since upper portion (256) of central nose (250) extends at least partially along the length of each sled rail (230, 232, 233), upper portion (256) may horizontally stabilize inner walls (71) of cartridge body (70) at the same longitudinal positions at which sled rails (230, 232, 233) are located while wedge sled (210) moves longitudinally through staple cartridge (37). In this manner, central nose (250) may provide horizontal stability to cartridge body (70) at longitudinal positions corresponding to each staple aperture (51) along the length of cartridge body (70) substantially contemporaneously with (e.g., during at least a portion of the duration of) the corresponding sled rail (230, 232, 233) fully lifting the corresponding staple driver (43) to drive the corresponding staple (47) out through staple aperture (51). By providing horizontal stability to cartridge body (70) at such longitudinal positions substantially contemporaneously with fully lifting staple drivers (43) to drive staples (47) out through staple apertures (51) at such longitudinal positions, central nose (250) may promote proper alignment of each staple aperture (51) with the corresponding staple forming pocket (53) on the inner surface of anvil (18) while deploying and forming each staple (47). For example, central nose (250) may promote vertical and/or angular alignment of each staple aperture (51) with the corresponding staple forming pocket (53) by inhibiting lateral deflection of inner walls (71) which might otherwise cause staple apertures (51) to be angled (e.g., laterally inwardly or laterally outwardly) relative to the corresponding staple forming pocket (53). As discussed above, sled rails (230, 232, 233) may themselves horizontally stabilize corresponding walls (71) of cartridge body (70) at their respective longitudinal positions, and thus may also promote vertical and/or angular alignment of each staple aperture (51) with the corresponding staple forming pocket (53) by inhibiting lateral deflection of inner walls (71) which might otherwise cause staple apertures (51) to be angled (e.g., laterally inwardly or laterally outwardly) relative to the corresponding staple forming pocket (53). Therefore, central nose (250) and sled rails (230, 232, 233) may cooperatively provide horizontal stability to cartridge body (70) at the respective longitudinal positions of each sled rail (230, 232, 233) while wedge sled (210) moves longitudinally through staple cartridge (37). It should be understood that anvil (18) is intentionally omitted from the view in FIG. 13.

Wedge sled (210) may be formed of any suitable material or combination of materials, including but not limited to metallic materials such as stainless steel (e.g., hardened stainless steel) or titanium. In some versions, wedge sled (210) may be manufactured via a metal injection molding (MIM) process. It will be appreciated that such a MIM process may provide wedge sled (210) with improved compression support and less lateral deflection, and may enable wedge sled (210) to provide improved rigidity to staple cartridge (37) during use (e.g., clamping and/or firing). Such a MIM process may include molding wedge sled (210) as a single unitary piece from a liquid MIM feedstock mix of metal powder and binder, for example. The MIM process may further include subjecting wedge sled (210) to various types of conditioning, including but not limited to cleaning, thermal debinding, and/or sintering.

In any event, after the MIM process is complete, all surfaces of wedge sled (210) may have an initial (e.g., raw MIM) surface finish, including top surfaces (218) of base platform (212), distal upper chamfers (224), and cam surfaces (240, 242, 244, 245, 246, 247) of sled rails (230, 232, 233). Such an initial surface finish may be rough, abrasive, and/or granular, and may generally be similar to the texture of pitted sandpaper. Thus, select surfaces of wedge sled (210) may be further conditioned to remove the initial surface finish from the select surfaces and provide the select surfaces with a final surface finish that is relatively smoother (e.g., finer, more polished) than the initial surface finish. For example, top surfaces (218) of base platform (212), distal upper chamfers (224), and cam surfaces (240, 242, 244, 245, 246, 247) of sled rails (230, 232, 233) may be machined to remove the initial surface finish from top surfaces (218), distal upper chamfers (224), and cam surfaces (240, 242, 244, 245, 246, 247) and provide top surfaces (218), distal upper chamfers (224), and cam surfaces (240, 242, 244, 245, 246, 247) with such a final surface finish. The final surface finish of top surfaces (218), distal upper chamfers (224), and cam surfaces (240, 242, 244, 245, 246, 247) may promote reduced friction and smooth interaction between top surfaces (218), distal upper chamfers (224), and cam surfaces (240, 242, 244, 245, 246, 247) and staple drivers (43) and thereby minimize wearing of the portions of staple drivers (43) contacted by top surfaces (218), distal upper chamfers (224), and cam surfaces (240, 242, 244, 245, 246, 247).

While the select surfaces provided with the final surface finish have been described in the form of top surfaces (218) of base platform (212), distal upper chamfers (224), and cam surfaces (240, 242, 244, 245, 246, 247) of sled rails (230, 232, 233), it will be appreciated that any other surfaces of wedge sled (210) may additionally or alternatively be provided with the final surface finish. For example, bottom surface (216) may be provided with the final surface finish to promote reduced friction and smooth interaction between bottom surface (216) and tray (74).

In some versions, the remaining, non-select surfaces of wedge sled (210) may not be further conditioned such that the initial surface finish may remain on the non-select surfaces during use (e.g., clamping and/or firing). For example, top surfaces (220) of raised platform (214) and/or ledge surfaces (262) of central nose (250) may retain the initial surface finish. As another example, every surface of wedge sled (210) other than top surfaces (218) of base platform (212), distal upper chamfers (224), and cam surfaces (240, 242, 244, 245, 246, 247) of sled rails (230, 232, 233) may retain the initial surface finish. Thus, the select surfaces of wedge sled (210) may have the final surface finish while the non-select surfaces of wedge sled (210) may have the initial surface finish, such that wedge sled (210) may have at least two distinct surface finishes.

The select and non-select surfaces may be determined based on the particular components of staple cartridge (37) and/or firing beam (14) with which each individual surface of wedge sled (210) interacts. In this regard, the final surface finish may be more desirable for surfaces of wedge sled (210) which interact with certain predetermined components of staple cartridge (37) and/or firing beam (14) than others. For example, top surfaces (218) of base platform (212), distal upper chamfers (224), and cam surfaces (240, 242, 244, 245, 246, 247) of sled rails (230, 232, 233) may be selected to receive the final surface finish based on their interaction with staple drivers (43), while the remaining surfaces of sled rails (230, 232, 233), top surfaces (220) of raised platform (214), and/or ledge surfaces (262) of central nose (250) may not be selected to receive the final surface finish based on their interaction with cartridge body (70). As another example, bottom surface (216) may be selected to receive the final surface finish based on its interaction with tray (74), while a proximal end surface of wedge sled (210) may not be selected to receive the final surface finish based on its interaction with pusher block (80).

Figure 14A:
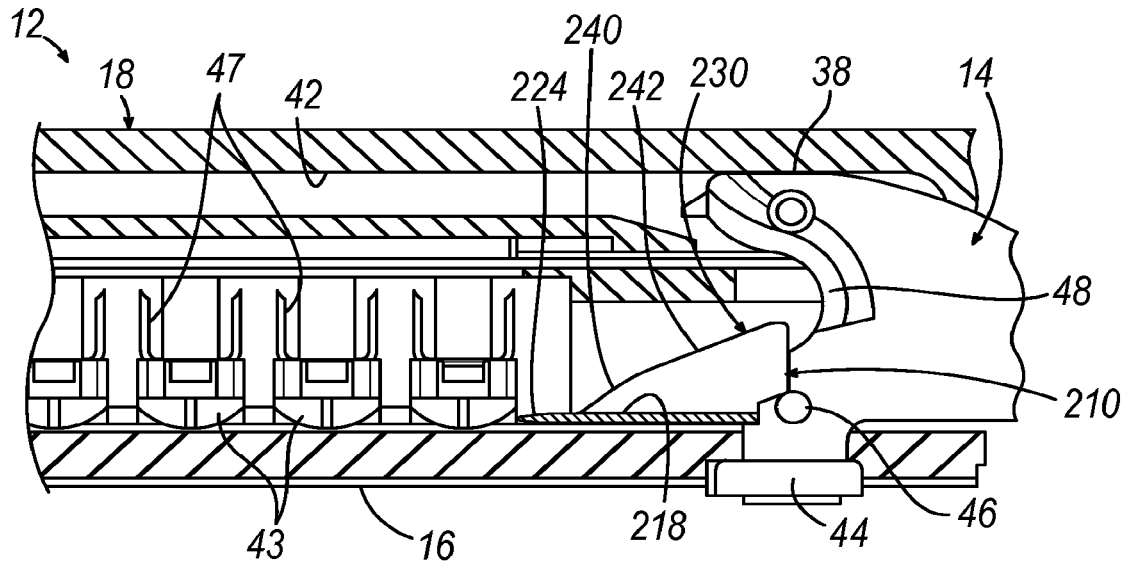
FIG. 14A depicts a side cross-sectional view of the end effector of FIG. 3, with the wedge sled of FIG. 11 captured between the cartridge body and the cartridge tray of the staple cartridge of the end effector, showing the wedge sled in a proximal position.
Figure 14B:
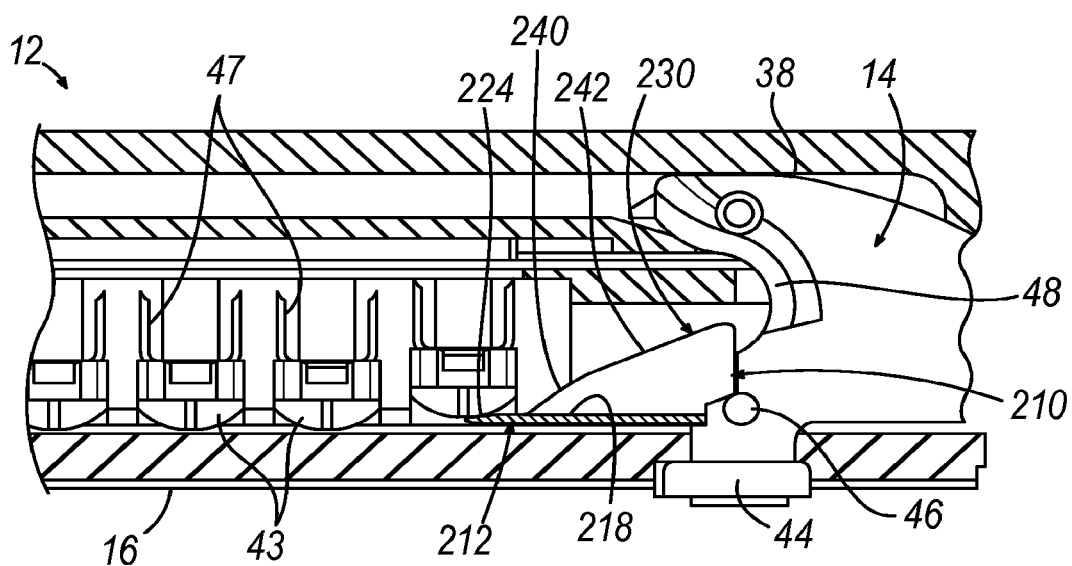
FIG. 14B depicts a side cross-sectional view of the end effector of FIG. 3, with the wedge sled of FIG. 11 captured between the cartridge body and the cartridge tray of the staple cartridge of the end effector, showing a distal chamfer of the wedge sled partially lifting a corresponding staple driver during distal translation of the wedge sled.
Figure 14C:
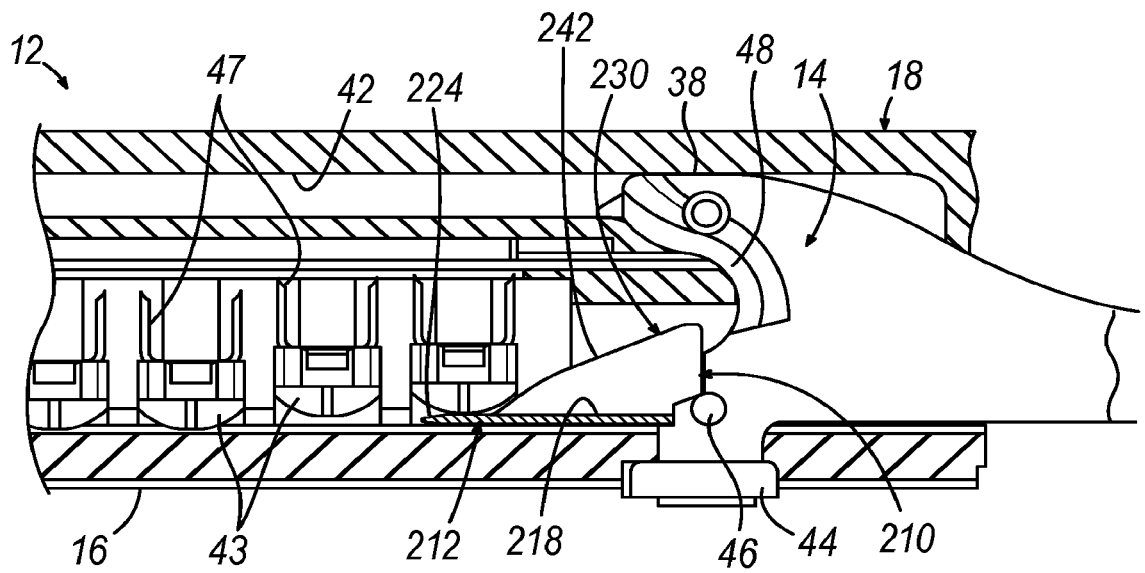
FIG. 14C depicts a side cross-sectional view of the end effector of FIG. 3, with the wedge sled of FIG. 11 captured between the cartridge body and the cartridge tray of the staple cartridge of the end effector, showing a top surface of a base of the wedge sled vertically supporting the corresponding staple driver during distal translation of the wedge sled.
Figure 14D:
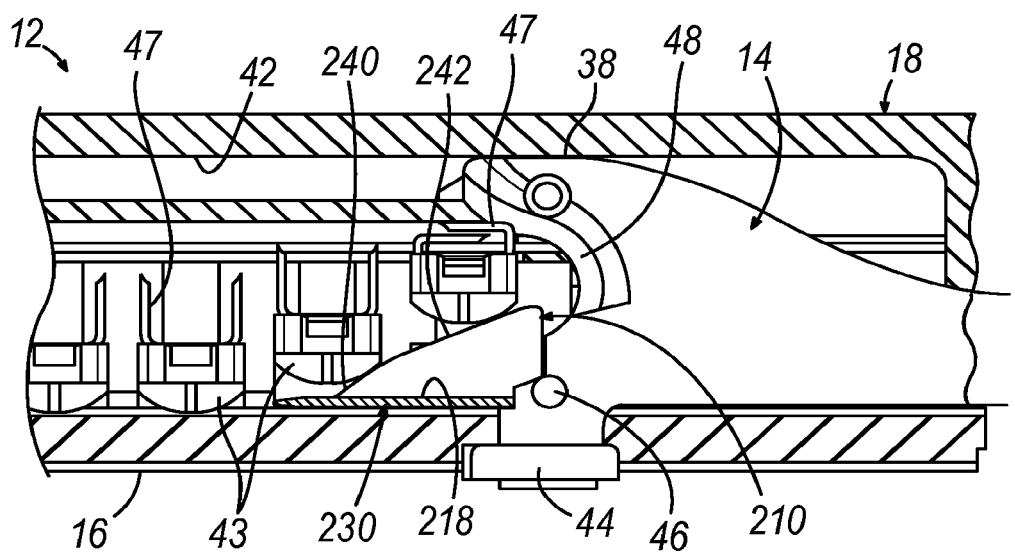
FIG. 14D depicts a side cross-sectional view of the end effector of FIG. 3, with the wedge sled of FIG. 11 captured between the cartridge body and the cartridge tray of the staple cartridge of the end effector, showing a cam surface of a sled rail of the wedge sled fully lifting the corresponding staple driver during distal translation of the wedge sled.

Referring now to FIGS. 14A-14D, during firing, wedge sled (210) is driven distally from a proximal position shown in FIG. 14A into upward camming contact with staple drivers (43) that in turn drive staples (47) out through staple apertures (51) and into forming contact with staple forming pockets (53) on the inner surface of anvil (18). More particularly, distal upper chamfer (224) of base platform (212) cammingly engages a respective staple driver (43) during distal translation of wedge sled (210) to lift the respective staple driver (43) above tray (74), as shown in FIG. 14B. For example, distal upper chamfer (224) may lift the respective staple driver (43) to a first height onto the respective top surface (218) of base platform (212) without ejecting the corresponding staple (47) through the corresponding staple aperture (51). Thus, distal upper chamfer (224) may be considered to "partially" lift the respective staple driver (43). Top surface (218) then vertically supports the respective staple driver (43) during continued distal translation of wedge sled (210), as shown in FIG. 14C. For example, top surface (218) may temporarily maintain the respective staple driver (43) at the first height. Cam surfaces (240, 242, 244, 245, 246, 247) of the respective sled rail (230, 232) then cammingly engage the respective staple driver (43) during further distal translation of wedge sled (210) to lift the respective staple driver (43) above the respective top surface (218) of base platform (212), as shown in FIG. 14D. For example, cam surfaces (240, 242, 244, 245, 246, 247) may lift the respective staple driver (43) to a second height greater than the first height to eject the corresponding staple (47) through the corresponding staple aperture (51) and into forming contact with the corresponding staple forming pocket (53). Thus, cam surfaces (240, 242, 244, 245, 246, 247) may be considered to "fully" lift the respective staple driver (43). It should be understood that staple forming pockets (53) are intentionally omitted from the view in FIGS. 14A-14D.

IV. EXEMPLARY SLEDS HAVING CARTRIDGE BIASING FEATURES

In some instances, it may be desirable to provide a wedge sled that is configured to provide further horizontal stability to staple cartridge (37) by biasing the walls of cartridge body (70) adjacent to the wedge sled laterally inwardly. FIGS. 15-19 show exemplary wedge sleds (310, 410, 510, 610, 710) which each provide such functionalities. Wedge sleds (310, 410, 510, 610, 710) are each similar to wedge sled (110) and/or wedge sled (210) described above except as otherwise described below. For example, wedge sleds (310, 410, 510, 610, 710) each occupy the same amount of space longitudinally within staple cartridge (37) as wedge sleds (41, 110, 210), making wedge sleds (310, 410, 510, 610, 710) substantially interchangeable with wedge sleds (41, 110, 210).

A. Exemplary Sled Having Toed-In Inner and Outer Sled Rails and Undercuts

Figure 15:
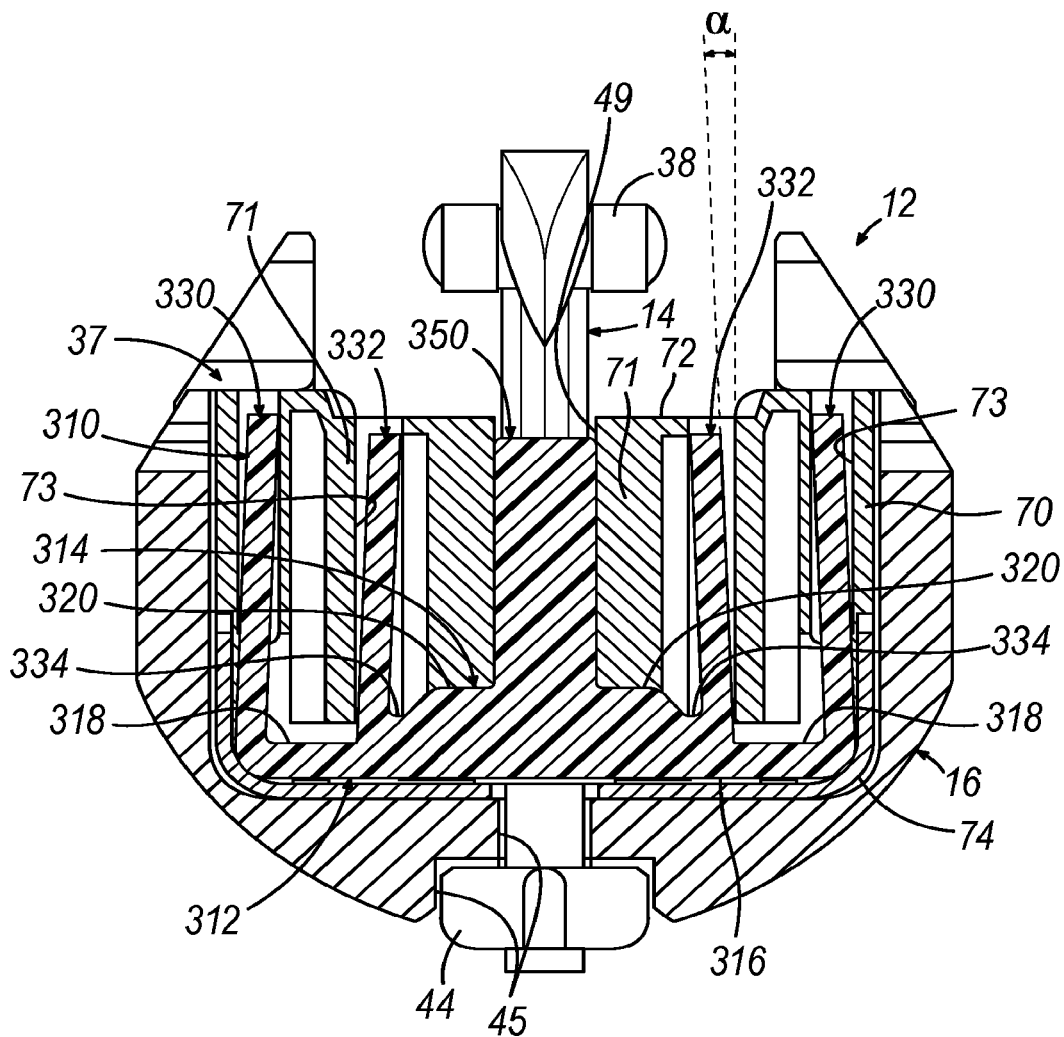
FIG. 15 depicts an end cross-sectional view of the end effector of FIG. 3 with another exemplary wedge sled captured between the cartridge body and the cartridge tray of the staple cartridge of the end effector, showing the wedge sled having toed-in inner and outer sled rails and undercuts.

FIG. 15 depicts an exemplary wedge sled (310) comprising a base including a base platform (312) and a central raised platform (314) extending upwardly from base platform (312). In the example shown, base platform (312) has a substantially flat bottom surface (316) defining a horizontal plane and configured to slide longitudinally along tray (74) while wedge sled (310) moves longitudinally through staple cartridge (37). Base platform (312) also has a laterally-opposed pair of substantially flat top surfaces (318) parallel to bottom surface (316), and raised platform (314) similarly has a laterally-opposed pair of substantially flat top surfaces (320) parallel to bottom surface (316). As shown, top surfaces (318, 320) are configured to confront and/or slidably contact or otherwise engage respective bottom surfaces of corresponding walls (71) of cartridge body (70) to thereby vertically support the corresponding walls (71) while wedge sled (310) moves longitudinally through staple cartridge (37).

Wedge sled (310) further comprises a laterally-opposed pair of outer sled rails (330) extending upwardly from base platform (312), and a laterally-opposed pair of inner sled rails (332) extending upwardly from both base platform (312) and raised platform (314). Sled rails (330, 332) may also be referred to as "cam ramps" or "cam wedges." Sled rails (330, 332) of the present version are each tilted or bent laterally inwardly from the respective top surfaces (318, 320) of base platform (312) and raised platform (314), such that sled rails (330, 332) are obliquely oriented relative to the horizontal plane and relative to a vertical-longitudinal plane. More particularly, each sled rail (330, 332) is bent laterally inwardly at a same oblique angle ($\alpha$) relative to the vertical-longitudinal plane (or to any plane parallel thereto), such that sled rails (330, 332) on each side of the vertical-longitudinal plane are parallel to each other and such that wedge sled (310) is substantially symmetric about the vertical-longitudinal plane, at least with respect to the configurations of sled rails (330, 332). In some versions, oblique angle ($\alpha$) may be approximately 7.5°. Alternatively, any other suitable angle may be used. In the example shown, wedge sled (310) includes a laterally-opposed pair of recesses (334) extending downwardly from top surfaces (320) of raised platform (314) adjacent to the corresponding inner sled rails (332) to assist with facilitating the laterally-inwardly bent configurations of inner sled rails (332). Recesses (334) may also be referred to as "undercuts." In some versions, recesses (334) may each extend at least partially along the length of the respective inner sled rail (332).

As shown, sled rails (330, 332) are configured to be received within corresponding longitudinally-extending slots (73) of cartridge body (70), and to slidably contact or otherwise engage respective side surfaces of corresponding walls (71) of cartridge body (70) to thereby horizontally stabilize walls (71) while wedge sled (310) moves longitudinally through staple cartridge (37). For example, outer and inner sled rails (330, 332) may inhibit laterally inward and/or laterally outward deflection (e.g., bending) of walls (71). In this regard, the laterally-inwardly bent configurations of sled rails (330, 332) of the present version may be particularly suitable for inhibiting laterally outward deflection of walls (71). For example, sled rails (330, 332) of the present version may bias the corresponding walls (71) toward a substantially vertical orientation by counteracting any laterally-outwardly directed forces that might be applied to walls (71) during use (e.g., clamping and/or firing). In this regard, oblique angle ($\alpha$) may be selected to achieve a desired amount of laterally-inwardly directed force applied by each sled rail (330, 332) to the corresponding wall (71) sufficient to overcome such laterally-outwardly directed forces while causing limited or no laterally-inward bending of the corresponding wall (71). Likewise, sled rails (330, 332) may each be attached to base platform (312) and raised platform (314), respectively, with a predetermined amount of flexibility to minimize laterally-inward bending of the corresponding wall (71) by allowing sled rails (330, 332) to be resiliently urged laterally outwardly upon application of a threshold force thereto. Thus, sled rails (330, 332) may be considered to be resiliently biased laterally inwardly. In some versions, sled rails (330, 332) may additionally or alternatively be configured to slidably contact or otherwise engage respective upper slot surfaces of corresponding slots (73) of cartridge body (70) to thereby vertically support upper deck (72) while wedge sled (310) moves longitudinally through staple cartridge (37).

Wedge sled (310) further comprises a central nose (350) extending upwardly from raised platform (314) between inner sled rails (332). In the example shown, central nose (350) is laterally spaced apart from each recess (334) to define top surfaces (320) of raised platform (314).

As shown, central nose (350) is configured to be at least partially received within vertical slot (49) of staple cartridge (37). In some versions, central nose (350) is configured to slidably contact or otherwise engage inner walls (71) of cartridge body (70) to thereby vertically support and/or horizontally stabilize inner walls (71) while wedge sled (310) moves longitudinally through staple cartridge (37), as described above with respect to central noses (150, 250). For example, central nose (350) may inhibit laterally inward deflection (e.g., bending) of inner walls (71) which might otherwise be caused by the laterally-inwardly directed forces applied to inner walls (71) by the corresponding inner sled rails (332). Likewise, inner sled rails (332) may inhibit laterally inward deflection (e.g., bending) of outer walls (71) which might otherwise be caused by the laterally-inwardly directed forces applied to outer walls (71) by the corresponding outer sled rails (330). In some versions, some laterally inward deflection of inner and/or outer walls (71) may be permitted which does not deform the overall exterior shape of staple cartridge (37) and, more particularly, which does not cause misalignment of staple apertures (51) relative to the corresponding staple forming pockets (53). Thus, central nose (350) and sled rails (330, 332) may cooperatively provide improved horizontal stability to cartridge body (70) at the respective longitudinal positions of each sled rail (330, 332) while wedge sled (310) moves longitudinally through staple cartridge (37). It should be understood that anvil (18) is intentionally omitted from the view in FIG. 15.

B. Exemplary Sled Having Toed-In Inner and Outer Sled Rails

Figure 16:
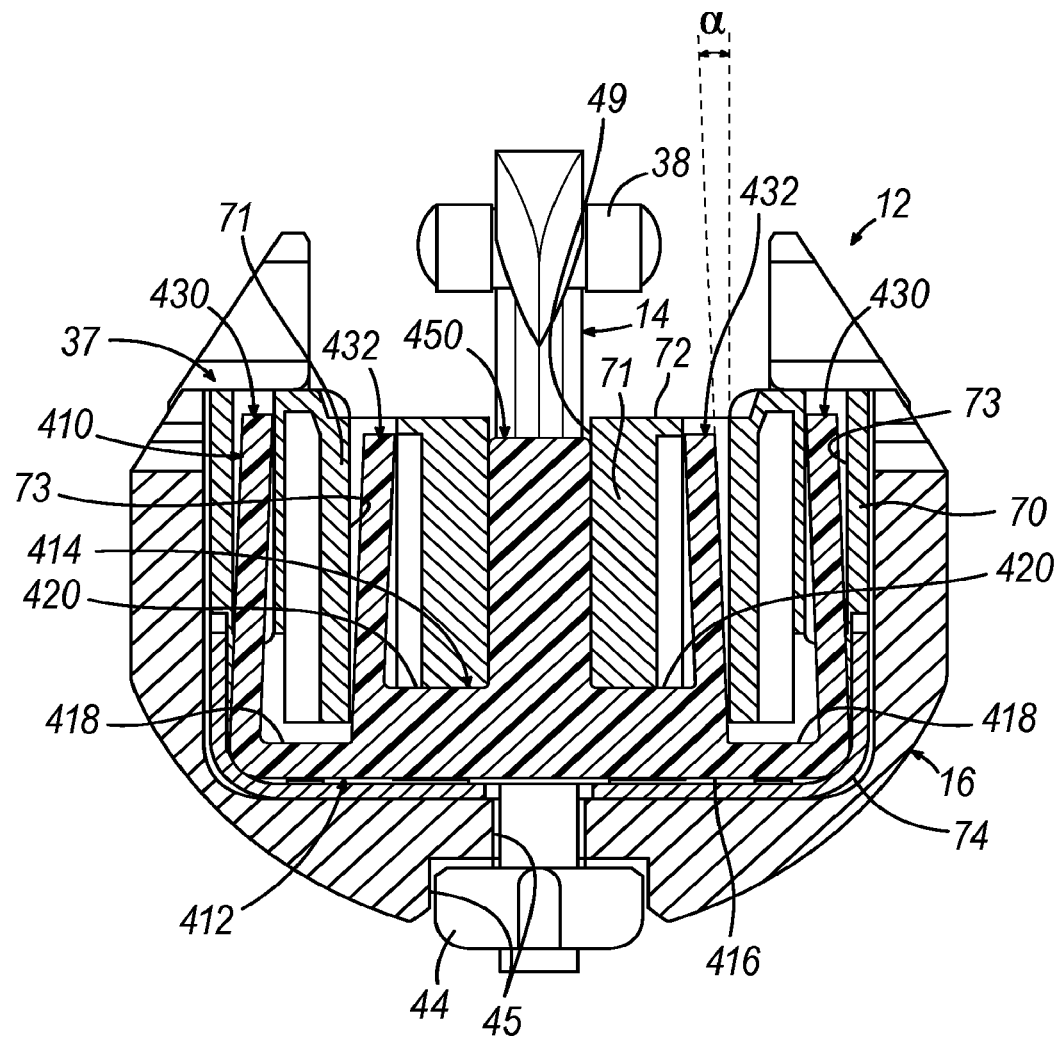
FIG. 16 depicts an end cross-sectional view of the end effector of FIG. 3 with another exemplary wedge sled captured between the cartridge body and the cartridge tray of the staple cartridge of the end effector, showing the wedge sled having toed-in inner and outer sled rails.

FIG. 16 depicts an exemplary wedge sled (410) comprising a base including a base platform (412) and a central raised platform (414) extending upwardly from base platform (412). In the example shown, base platform (412) has a substantially flat bottom surface (416) defining a horizontal plane and configured to slide longitudinally along tray (74) while wedge sled (410) moves longitudinally through staple cartridge (37). Base platform (412) also has a laterally-opposed pair of substantially flat top surfaces (418) parallel to bottom surface (416), and raised platform (414) similarly has a laterally-opposed pair of substantially flat top surfaces (420) parallel to bottom surface (416). As shown, top surfaces (418, 420) are configured to confront and/or slidably contact or otherwise engage respective bottom surfaces of corresponding walls (71) of cartridge body (70) to thereby vertically support the corresponding walls (71) while wedge sled (410) moves longitudinally through staple cartridge (37).

Wedge sled (410) further comprises a laterally-opposed pair of outer sled rails (430) extending upwardly from base platform (412), and a laterally-opposed pair of inner sled rails (432) extending upwardly from both base platform (412) and raised platform (414). Sled rails (430, 432) may also be referred to as "cam ramps" or "cam wedges." Sled rails (430, 432) of the present version are each tilted or bent laterally inwardly from the respective top surfaces (418, 420) of base platform (412) and raised platform (414), such that sled rails (430, 432) are obliquely oriented relative to the horizontal plane and relative to a vertical-longitudinal plane. More particularly, each sled rail (430, 432) is bent laterally inwardly at a same oblique angle ($\alpha$) relative to the vertical-longitudinal plane (or to any plane parallel thereto), such that sled rails (430, 432) on each side of the vertical-longitudinal plane are parallel to each other and such that wedge sled (410) is substantially symmetric about the vertical-longitudinal plane, at least with respect to the configurations of sled rails (430, 432). In some versions, oblique angle ($\alpha$) may be approximately 7.5°. Alternatively, any other suitable angle may be used.

As shown, sled rails (430, 432) are configured to be received within corresponding longitudinally-extending slots (73) of cartridge body (70), and to slidably contact or otherwise engage respective side surfaces of corresponding walls (71) of cartridge body (70) to thereby horizontally stabilize walls (71) while wedge sled (410) moves longitudinally through staple cartridge (37). For example, outer and inner sled rails (430, 432) may inhibit laterally inward and/or laterally outward deflection (e.g., bending) of walls (71). In this regard, the laterally-inwardly bent configurations of sled rails (430, 432) of the present version may be particularly suitable for inhibiting laterally outward deflection of walls (71). For example, sled rails (430, 432) of the present version may bias the corresponding walls (71) toward a substantially vertical orientation by counteracting any laterally-outwardly directed forces that might be applied to walls (71) during use (e.g., clamping and/or firing). In this regard, oblique angle ($\alpha$) may be selected to achieve a desired amount of laterally-inwardly directed force applied by each sled rail (430, 432) to the corresponding wall (71) sufficient to overcome such laterally-outwardly directed forces while causing limited or no laterally-inward bending of the corresponding wall (71). Likewise, sled rails (430, 432) may each be attached to base platform (412) and raised platform (414), respectively, with a predetermined amount of flexibility to minimize laterally-inward bending of the corresponding wall (71) by allowing sled rails (430, 432) to be resiliently urged laterally outwardly upon application of a threshold force thereto. Thus, sled rails (430, 432) may be considered to be resiliently biased laterally inwardly. In some versions, sled rails (430, 432) may additionally or alternatively be configured to slidably contact or otherwise engage respective upper slot surfaces of corresponding slots (73) of cartridge body (70) to thereby vertically support upper deck (72) while wedge sled (410) moves longitudinally through staple cartridge (37).

Wedge sled (410) further comprises a central nose (450) extending upwardly from raised platform (414) between inner sled rails (432). In the example shown, central nose (450) is laterally spaced apart from each inner sled rail (432) to define top surfaces (420) of raised platform (414). More particularly, central nose (450) is equally spaced apart from inner sled rails (432).

As shown, central nose (450) is configured to be at least partially received within vertical slot (49) of staple cartridge (37). In some versions, central nose (450) is configured to slidably contact or otherwise engage inner walls (71) of cartridge body (70) to thereby vertically support and/or horizontally stabilize inner walls (71) while wedge sled (410) moves longitudinally through staple cartridge (37), as described above with respect to central noses (150, 250). For example, central nose (450) may inhibit laterally inward deflection (e.g., bending) of inner walls (71) which might otherwise be caused by the laterally-inwardly directed forces applied to inner walls (71) by the corresponding inner sled rails (432). Likewise, inner sled rails (432) may inhibit laterally inward deflection (e.g., bending) of outer walls (71) which might otherwise be caused by the laterally-inwardly directed forces applied to outer walls (71) by the corresponding outer sled rails (430). In some versions, some laterally inward deflection of inner and/or outer walls (71) may be permitted which does not deform the overall exterior shape of staple cartridge (37) and, more particularly, which does not cause misalignment of staple apertures (51) relative to the corresponding staple forming pockets (53). Thus, central nose (450) and sled rails (430, 432) may cooperatively provide improved horizontal stability to cartridge body (70) at the respective longitudinal positions of each sled rail (430, 432) while wedge sled (410) moves longitudinally through staple cartridge (37). It should be understood that anvil (18) is intentionally omitted from the view in FIG. 16.

C. Exemplary Sled Having Toed-In Inner Sled Rails

Figure 17:
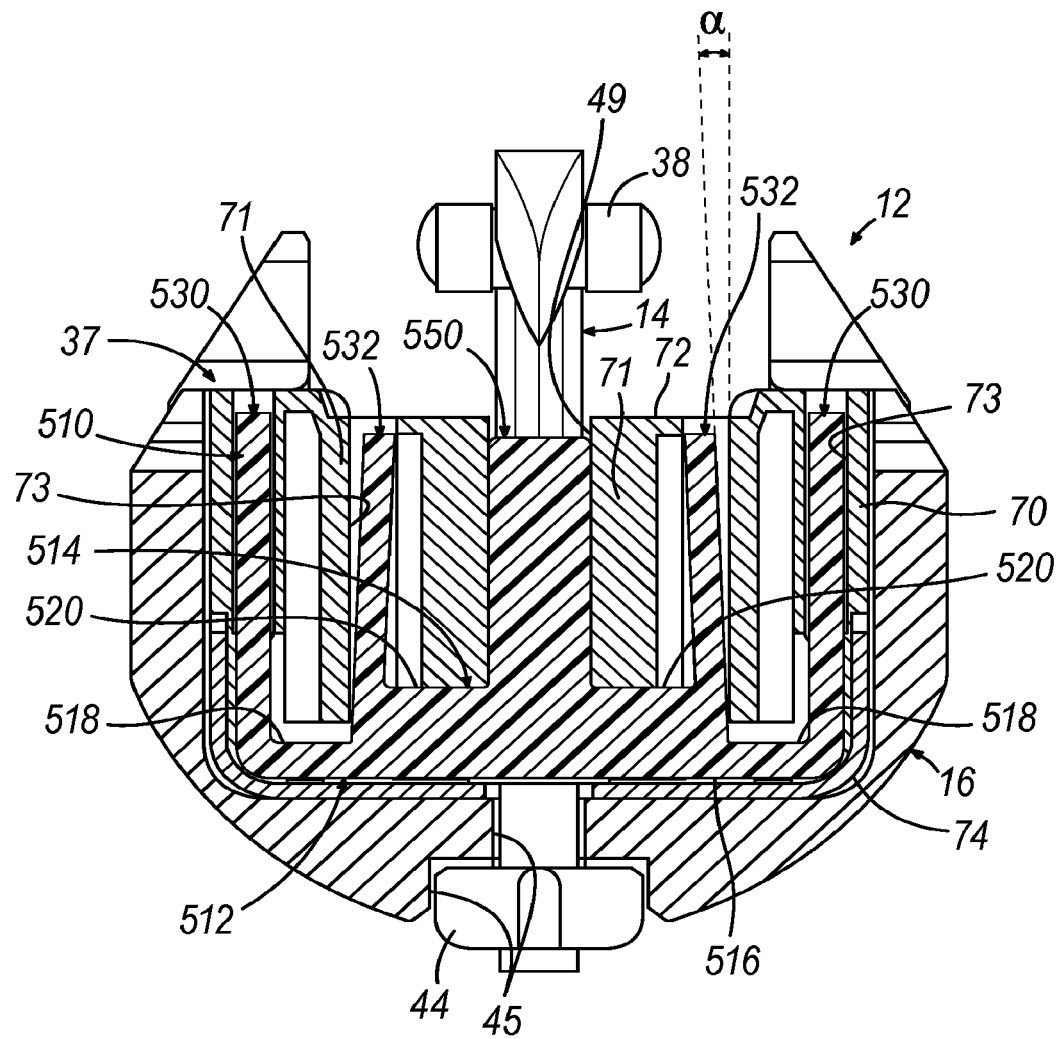
FIG. 17 depicts an end cross-sectional view of the end effector of FIG. 3 with another exemplary wedge sled captured between the cartridge body and the cartridge tray of the staple cartridge of the end effector, showing the wedge sled having toed-in inner sled rails.

FIG. 17 depicts an exemplary wedge sled (510) comprising a base including a base platform (512) and a central raised platform (514) extending upwardly from base platform (512). In the example shown, base platform (512) has a substantially flat bottom surface (516) defining a horizontal plane and configured to slide longitudinally along tray (74) while wedge sled (510) moves longitudinally through staple cartridge (37). Base platform (512) also has a laterally-opposed pair of substantially flat top surfaces (518) parallel to bottom surface (516), and raised platform (514) similarly has a laterally-opposed pair of substantially flat top surfaces (520) parallel to bottom surface (516). As shown, top surfaces (518, 520) are configured to confront and/or slidably contact or otherwise engage respective bottom surfaces of corresponding walls (71) of cartridge body (70) to thereby vertically support the corresponding walls (71) while wedge sled (510) moves longitudinally through staple cartridge (37).

Wedge sled (510) further comprises a laterally-opposed pair of outer sled rails (530) extending upwardly from base platform (512), and a laterally-opposed pair of inner sled rails (532) extending upwardly from both base platform (512) and raised platform (514). Sled rails (530, 532) may also be referred to as "cam ramps" or "cam wedges." Outer sled rails (530) of the present version extend substantially straight and upright from the respective top surfaces (518) of base platform (512), such that outer sled rails (530) are perpendicularly oriented relative to the horizontal plane and parallel to a vertical-longitudinal plane. Inner sled rails (532) of the present version are each tilted or bent laterally inwardly from the respective top surfaces (520) of raised platform (514), such that inner sled rails (532) are obliquely oriented relative to the horizontal plane and relative to a vertical-longitudinal plane. More particularly, each inner sled rail (532) is bent laterally inwardly at an oblique angle ($\alpha$) relative to the vertical-longitudinal plane (or to any plane parallel thereto), such that inner sled rails (532) are each obliquely oriented relative to the adjacent outer sled rail (530) and such that wedge sled (510) is substantially symmetric about the vertical-longitudinal plane, at least with respect to the configurations of sled rails (530, 532). In some versions, oblique angle ($\alpha$) may be approximately 7.5°. Alternatively, any other suitable angle may be used.

As shown, sled rails (530, 532) are configured to be received within corresponding longitudinally-extending slots (73) of cartridge body (70), and to slidably contact or otherwise engage respective side surfaces of corresponding walls (71) of cartridge body (70) to thereby horizontally stabilize walls (71) while wedge sled (510) moves longitudinally through staple cartridge (37). For example, outer and inner sled rails (530, 532) may inhibit laterally inward and/or laterally outward deflection (e.g., bending) of walls (71). In this regard, the laterally-inwardly bent configurations of inner sled rails (532) of the present version may be particularly suitable for inhibiting laterally outward deflection of inner walls (71). For example, inner sled rails (532) of the present version may bias the corresponding inner walls (71) toward a substantially vertical orientation by counteracting any laterally-outwardly directed forces that might be applied to inner walls (71) during use (e.g., clamping and/or firing). In this regard, oblique angle ($\alpha$) may be selected to achieve a desired amount of laterally-inwardly directed force applied by each inner sled rail (532) to the corresponding inner wall (71) sufficient to overcome such laterally-outwardly directed forces while causing limited or no laterally-inward bending of the corresponding wall (71). Likewise, inner sled rails (532) may each be attached to raised platform (514) with a predetermined amount of flexibility to minimize laterally-inward bending of the corresponding wall (71) by allowing inner sled rails (532) to be resiliently urged laterally outwardly upon application of a threshold force thereto. Thus, inner sled rails (532) may be considered to be resiliently biased laterally inwardly. In some versions, sled rails (530, 532) may additionally or alternatively be configured to slidably contact or otherwise engage respective upper slot surfaces of corresponding slots (73) of cartridge body (70) to thereby vertically support upper deck (72) while wedge sled (510) moves longitudinally through staple cartridge (37).

Wedge sled (510) further comprises a central nose (550) extending upwardly from raised platform (514) between inner sled rails (532). In the example shown, central nose (550) is laterally spaced apart from each inner sled rail (532) to define top surfaces (520) of raised platform (514). More particularly, central nose (550) is equally spaced apart from inner sled rails (532).

As shown, central nose (550) is configured to be at least partially received within vertical slot (49) of staple cartridge (37). In some versions, central nose (550) is configured to slidably contact or otherwise engage inner walls (71) of cartridge body (70) to thereby vertically support and/or horizontally stabilize inner walls (71) while wedge sled (510) moves longitudinally through staple cartridge (37), as described above with respect to central noses (150, 250). For example, central nose (550) may inhibit laterally inward deflection (e.g., bending) of inner walls (71) which might otherwise be caused by the laterally-inwardly directed forces applied to inner walls (71) by the corresponding inner sled rails (532). Likewise, inner sled rails (532) may inhibit laterally inward deflection (e.g., bending) of outer walls (71) which might otherwise be caused by the laterally-inwardly directed forces applied to outer walls (71) by the corresponding outer sled rails (530). In some versions, some laterally inward deflection of inner and/or outer walls (71) may be permitted which does not deform the overall exterior shape of staple cartridge (37) and, more particularly, which does not cause misalignment of staple apertures (51) relative to the corresponding staple forming pockets (53). Thus, central nose (550) and sled rails (530, 532) may cooperatively provide improved horizontal stability to cartridge body (70) at the respective longitudinal positions of each sled rail (530, 532) while wedge sled (510) moves longitudinally through staple cartridge (37). It should be understood that anvil (18) is intentionally omitted from the view in FIG. 17.

D. Exemplary Sled Having V-Shaped Base

Figure 18:
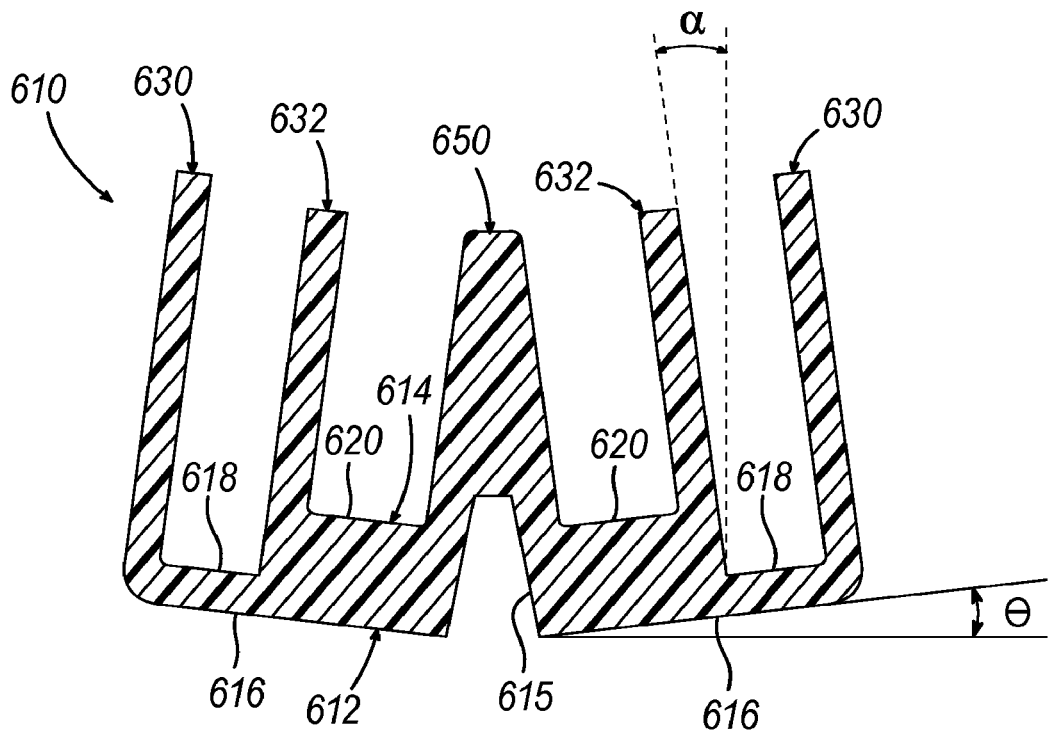
FIG. 18 depicts a cross-sectional view of another exemplary wedge sled having a V-shaped base.

FIG. 18 depicts an exemplary wedge sled (610) comprising a base including a base platform (612) and a central raised platform (614) extending upwardly from base platform (612). In the example shown, base platform (612) and raised platform (614) are each bifurcated by a longitudinally-extending inverted V-shaped slot (615) such that laterally-opposing halves of wedge sled (610) may each be tilted or bent laterally inwardly toward each other. In this regard, base platform (612) has a laterally-opposed pair of substantially flat bottom surfaces (616) obliquely oriented relative to a horizontal plane (e.g., collectively defined by lowermost, laterally-inner edges of bottom surfaces (616)). More particularly, each bottom surface (616) is bent laterally inwardly at a same oblique angle (θ) relative to the horizontal plane, such that base platform (612) has a generally V-shaped cross section and such that wedge sled (610) is substantially symmetric about the vertical-longitudinal plane, at least with respect to the configurations of bottom surfaces (616). Base platform (612) also has a laterally-opposed pair of substantially flat top surfaces (618) parallel to respective bottom surfaces (616), and raised platform (614) similarly has a laterally-opposed pair of substantially flat top surfaces (620) parallel to respective bottom surfaces (616). Top surfaces (618, 620) are configured to confront and/or slidably contact or otherwise engage respective bottom surfaces of corresponding walls (71) of cartridge body (70) to thereby vertically support the corresponding walls (71) while wedge sled (610) moves longitudinally through staple cartridge (37).

Wedge sled (610) further comprises a laterally-opposed pair of outer sled rails (630) extending upwardly from base platform (612), and a laterally-opposed pair of inner sled rails (632) extending upwardly from both base platform (612) and raised platform (614). Sled rails (630, 632) may also be referred to as "cam ramps" or "cam wedges." Sled rails (630, 632) of the present version extend substantially straight and upright from the respective top surfaces (618, 620) of base platform (612) and raised platform (614), such that sled rails (630, 632) are obliquely oriented relative to the horizontal plane and relative to a vertical-longitudinal plane via the oblique orientations of bottom surfaces (616) relative to the horizontal plane. More particularly, due to the laterally-inwardly bent configuration of base platform (612), each sled rail (630, 632) is bent laterally inwardly at a same oblique angle (α) relative to the vertical-longitudinal plane (or to any plane parallel thereto), such that sled rails (630, 632) on each side of the vertical-longitudinal plane are parallel to each other and such that wedge sled (610) is substantially symmetric about the vertical-longitudinal plane, at least with respect to the configurations of sled rails (630, 632). In some versions, oblique angle (α) may be approximately 7.5°. Alternatively, any other suitable angle may be used.

Sled rails (630, 632) are configured to be received within corresponding longitudinally-extending slots (73) of cartridge body (70), and to slidably contact or otherwise engage respective side surfaces of corresponding walls (71) of cartridge body (70) to thereby horizontally stabilize walls (71) while wedge sled (610) moves longitudinally through staple cartridge (37). For example, outer and inner sled rails (630, 632) may inhibit laterally inward and/or laterally outward deflection (e.g., bending) of walls (71). In this regard, the laterally-inwardly bent configurations of sled rails (630, 632) of the present version may be particularly suitable for inhibiting laterally outward deflection of walls (71). For example, sled rails (630, 632) of the present version may bias the corresponding walls (71) toward a substantially vertical orientation by counteracting any laterally-outwardly directed forces that might be applied to walls (71) during use (e.g., clamping and/or firing). In this regard, oblique angle (θ) and/or oblique angle (α) may be selected to achieve a desired amount of laterally-inwardly directed force applied by each sled rail (630, 632) to the corresponding wall (71) sufficient to overcome such laterally-outwardly directed forces while causing limited or no laterally-inward bending of the corresponding wall (71). Slot (615) may provide the laterally-opposing halves of wedge sled (610) with a predetermined amount of flexibility to minimize laterally-inward bending of the corresponding wall (71) by allowing sled rails (630, 632) to be resiliently urged laterally outwardly upon application of a threshold force thereto. Thus, sled rails (630, 632) may be considered to be resiliently biased laterally inwardly. In some versions, sled rails (630, 632) may additionally or alternatively be configured to slidably contact or otherwise engage respective upper slot surfaces of corresponding slots (73) of cartridge body (70) to thereby vertically support upper deck (72) while wedge sled (610) moves longitudinally through staple cartridge (37).

Wedge sled (610) further comprises a central nose (650) extending upwardly from raised platform (614) between inner sled rails (632). In the example shown, central nose (650) is laterally spaced apart from each recess (634) to define top surfaces (620) of raised platform (614).

Central nose (650) is configured to be at least partially received within vertical slot (49) of staple cartridge (37). In some versions, central nose (650) is configured to slidably contact or otherwise engage inner walls (71) of cartridge body (70) to thereby vertically support and/or horizontally stabilize inner walls (71) while wedge sled (610) moves longitudinally through staple cartridge (37), as described above with respect to central noses (150, 250). For example, central nose (650) may inhibit laterally inward deflection (e.g., bending) of inner walls (71) which might otherwise be caused by the laterally-inwardly directed forces applied to inner walls (71) by the corresponding inner sled rails (632). Likewise, inner sled rails (632) may inhibit laterally inward deflection (e.g., bending) of outer walls (71) which might otherwise be caused by the laterally-inwardly directed forces applied to outer walls (71) by the corresponding outer sled rails (630). In some versions, some laterally inward deflection of inner and/or outer walls (71) may be permitted which does not deform the overall exterior shape of staple cartridge (37) and, more particularly, which does not cause misalignment of staple apertures (51) relative to the corresponding staple forming pockets (53). Thus, central nose (650) and sled rails (630, 632) may cooperatively provide improved horizontal stability to cartridge body (70) at the respective longitudinal positions of each sled rail (630, 632) while wedge sled (610) moves longitudinally through staple cartridge (37).

E. Exemplary Sled Having Bifurcated Nose

Figure 19:
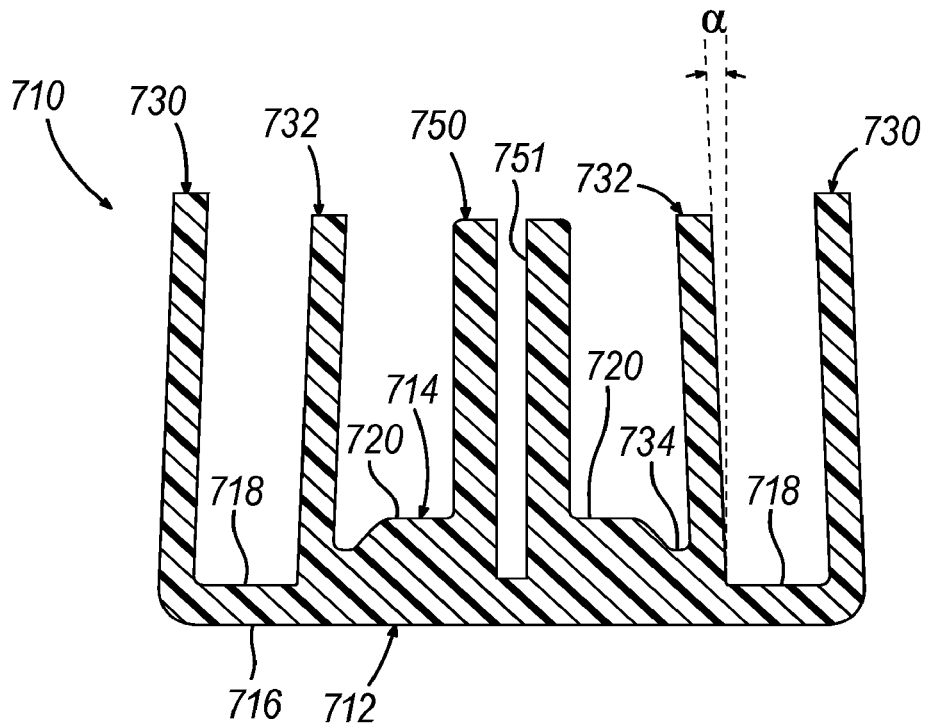
FIG. 19 depicts a cross-sectional view of another exemplary wedge sled having a bifurcated central nose.

FIG. 19 depicts an exemplary wedge sled (710) comprising a base including a base platform (712) and a central raised platform (714) extending upwardly from base platform (712). In the example shown, base platform (712) has a substantially flat bottom surface (716) defining a horizontal plane and configured to slide longitudinally along tray (74) while wedge sled (710) moves longitudinally through staple cartridge (37). Base platform (712) also has a laterally-opposed pair of substantially flat top surfaces (718) parallel to bottom surface (716), and raised platform (714) similarly has a laterally-opposed pair of substantially flat top surfaces (720) parallel to bottom surface (716). Top surfaces (718, 720) are configured to confront and/or slidably contact or otherwise engage respective bottom surfaces of corresponding walls (71) of cartridge body (70) to thereby vertically support the corresponding walls (71) while wedge sled (710) moves longitudinally through staple cartridge (37).

Wedge sled (710) further comprises a laterally-opposed pair of outer sled rails (730) extending upwardly from base platform (712), and a laterally-opposed pair of inner sled rails (732) extending upwardly from both base platform (712) and raised platform (714). Sled rails (730, 732) may also be referred to as "cam ramps" or "cam wedges." Sled rails (730, 732) of the present version are each tilted or bent laterally inwardly from the respective top surfaces (718, 720) of base platform (712) and raised platform (714), such that sled rails (730, 732) are obliquely oriented relative to the horizontal plane and relative to a vertical-longitudinal plane. More particularly, each sled rail (730, 732) is bent laterally inwardly at a same oblique angle ($\alpha$) relative to the vertical-longitudinal plane (or to any plane parallel thereto), such that sled rails (730, 732) on each side of the vertical-longitudinal plane are parallel to each other and such that wedge sled (710) is substantially symmetric about the vertical-longitudinal plane, at least with respect to the configurations of sled rails (730, 732). In some versions, oblique angle ($\alpha$) may be approximately 7.5°. Alternatively, any other suitable angle may be used. In the example shown, wedge sled (710) includes a laterally-opposed pair of recesses (734) extending downwardly from top surfaces (720) of raised platform (714) adjacent to the corresponding inner sled rails (732) to assist with facilitating the laterally-inwardly bent configurations of inner sled rails (732). Recesses (734) may also be referred to as "undercuts." In some versions, recesses (734) may each extend at least partially along the length of the respective inner sled rail (732).

Sled rails (730, 732) are configured to be received within corresponding longitudinally-extending slots (73) of cartridge body (70), and to slidably contact or otherwise engage respective side surfaces of corresponding walls (71) of cartridge body (70) to thereby horizontally stabilize walls (71) while wedge sled (710) moves longitudinally through staple cartridge (37). For example, outer and inner sled rails (730, 732) may inhibit laterally inward and/or laterally outward deflection (e.g., bending) of walls (71). In this regard, the laterally-inwardly bent configurations of sled rails (730, 732) of the present version may be particularly suitable for inhibiting laterally outward deflection of walls (71). For example, sled rails (730, 732) of the present version may bias the corresponding walls (71) toward a substantially vertical orientation by counteracting any laterally-outwardly directed forces that might be applied to walls (71) during use (e.g., clamping and/or firing). In this regard, oblique angle ($\alpha$) may be selected to achieve a desired amount of laterally-inwardly directed force applied by each sled rail (730, 732) to the corresponding wall (71) sufficient to overcome such laterally-outwardly directed forces while causing limited or no laterally-inward bending of the corresponding wall (71). Likewise, sled rails (730, 732) may each be attached to base platform (712) and raised platform (714), respectively, with a predetermined amount of flexibility to minimize laterally-inward bending of the corresponding wall (71) by allowing sled rails (730, 732) to be resiliently urged laterally outwardly upon application of a threshold force thereto. Thus, sled rails (730, 732) may be considered to be resiliently biased laterally inwardly. In some versions, sled rails (730, 732) may additionally or alternatively be configured to slidably contact or otherwise engage respective upper slot surfaces of corresponding slots (73) of cartridge body (70) to thereby vertically support upper deck (72) while wedge sled (710) moves longitudinally through staple cartridge (37).

Wedge sled (710) further comprises a central nose (750) extending upwardly from raised platform (714) between inner sled rails (732). In the example shown, central nose (750) is laterally spaced apart from each recess (734) to define top surfaces (720) of raised platform (714). In the present version, central nose (750) is bifurcated by a longitudinally-extending U-shaped slot (751) to facilitate laterally-inward deflection (e.g., bending) of central nose (750).

Central nose (750) is configured to be at least partially received within vertical slot (49) of staple cartridge (37). In some versions, central nose (750) is configured to slidably contact or otherwise engage inner walls (71) of cartridge body (70) to thereby vertically support and/or horizontally stabilize inner walls (71) while wedge sled (710) moves longitudinally through staple cartridge (37), as described above with respect to central noses (150, 250). For example, central nose (750) may inhibit laterally inward deflection (e.g., bending) of inner walls (71) which might otherwise be caused by the laterally-inwardly directed forces applied to inner walls (71) by the corresponding inner sled rails (732). Likewise, inner sled rails (732) may inhibit laterally inward deflection (e.g., bending) of outer walls (71) which might otherwise be caused by the laterally-inwardly directed forces applied to outer walls (71) by the corresponding outer sled rails (730). In some versions, some laterally inward deflection of inner and/or outer walls (71) may be permitted which does not deform the overall exterior shape of staple cartridge (37) and, more particularly, which does not cause misalignment of staple apertures (51) relative to the corresponding staple forming pockets (53). In this regard, central nose (750) may bend laterally-inwardly to accommodate such permitted laterally inward deflection of inner walls (71). Thus, central nose (750) and sled rails (730, 732) may cooperatively provide improved horizontal stability to cartridge body (70) at the respective longitudinal positions of each sled rail (730, 732) while wedge sled (710) moves longitudinally through staple cartridge (37).

While wedge sleds (110, 210, 310, 410, 510, 610, 710) of the present versions are shown and described herein in connection with staple cartridges configured for use with laparoscopic surgical staplers, such as staple cartridge (37), it will be appreciated that wedge sleds (110, 210, 310, 410, 510, 610, 710) of other versions may be adapted for use with staple cartridges configured for use with non-laparoscopic surgical staplers in open surgical procedures. Examples of such non-laparoscopic surgical staplers are disclosed in U.S. Pat. Pub. No. 2020/0046350, entitled "Firing System for Linear Surgical Stapler," published on Feb. 13, 2020, issued as U.S. Pat. No. 10,898,187 on Jan. 26, 2021; U.S. Pat. Pub. No. 2020/0046351, entitled "Decoupling Mechanism for Linear Surgical Stapler," published on Feb. 13, 2020, issued as U.S. Pat. No. 11,033,266 on Jun. 15, 2021; U.S. Pat. Pub. No. 2020/0046353, entitled "Clamping Assembly for Linear Surgical Stapler," published on Feb. 13, 2020; and U.S. application Ser. No. 16/537,005, entitled "Linear Surgical Stapler," filed Aug. 9, 2019, published as U.S. Pub. No. 2021/0038223 on Feb. 11, 2021. The disclosures of these references are incorporated by reference herein.

V. EXEMPLARY BIASING FEATURES INTEGRATED INTO CARTRIDGE

Figure 20:
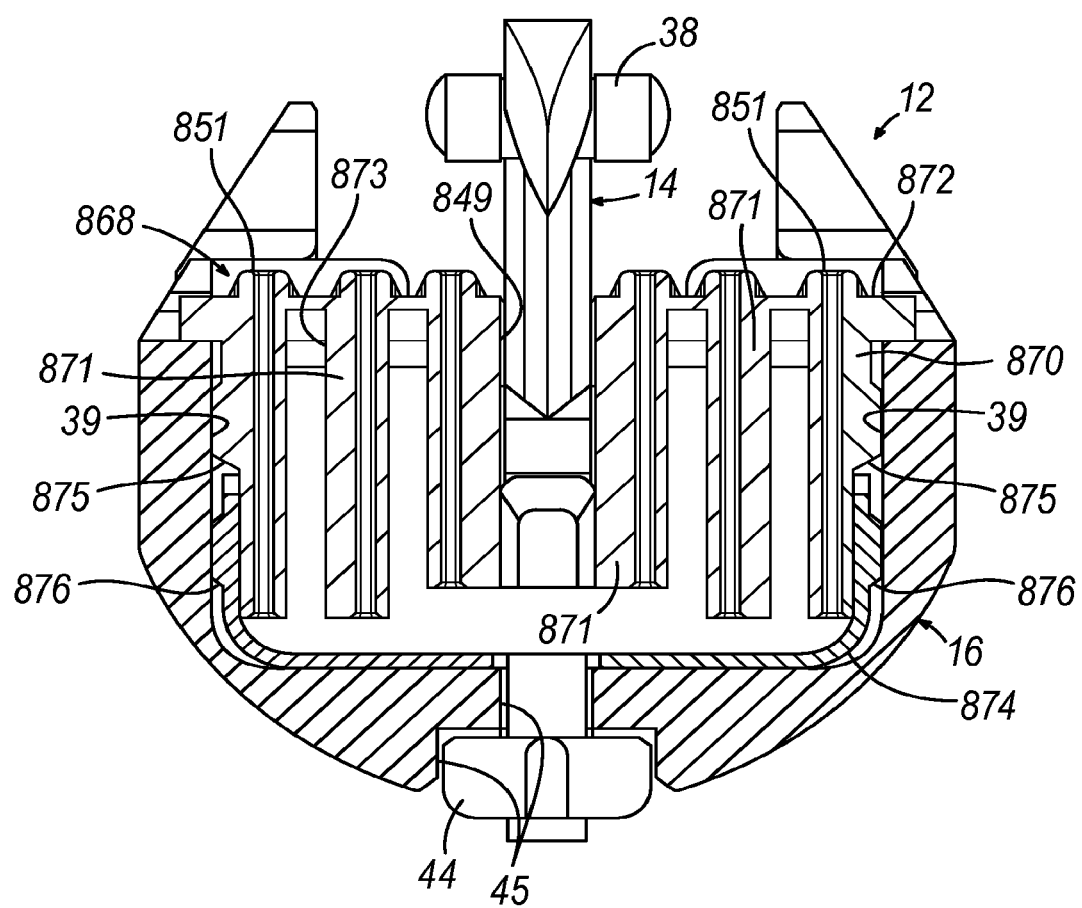
FIG. 20 depicts an end cross-sectional view of the end effector of FIG. 3 with an exemplary staple cartridge removably installed into a channel of a lower jaw of the end effector, showing the staple cartridge having various biasing features.

In some instances, it may be desirable to provide a staple cartridge that possesses improved horizontal stability as compared to staple cartridge (37) by biasing the walls of the cartridge body adjacent to wedge sled (41) laterally inwardly. FIG. 20 shows an exemplary staple cartridge (868)

which provides such functionality. Staple cartridge (868) is similar to staple cartridge (37) described above except as otherwise described below. For example, staple cartridge (37) is configured to be removably installed into a channel (39) of lower jaw (16).

As shown, staple cartridge (868) of this example includes a cartridge body (870) having a plurality of walls (871), and which presents an upper deck (872). Cartridge body (870) further has a plurality of longitudinally-extending slots (873) positioned between respective walls (871). Cartridge body (870) is coupled with a lower cartridge tray (874). As shown, a vertical slot (849) is formed through part of staple cartridge (868). Three rows of staple apertures (851) are formed through upper deck (872) on one side of vertical slot (849), with another set of three rows of staple apertures (851) being formed through upper deck (872) on the other side of vertical slot (849).

In the present version, cartridge body (870) includes a laterally-opposed pair of upper protrusions (875) extending laterally outwardly from opposing sides of cartridge body (870) above tray (874). Likewise, tray (874) includes a laterally-opposed pair of lower protrusions (876) extending laterally outwardly from opposing sides of tray (874). Protrusions (875, 876) are configured to abut or otherwise engage respective side surfaces of channel (39) of lower jaw (16) to thereby horizontally stabilize walls (871) while a wedge sled (not shown), such as any of wedge sleds (41, 110, 210, 310, 410, 510, 610, 710) described above, moves longitudinally through staple cartridge (37). For example, protrusions (875, 876) may inhibit laterally outward deflection (e.g., bending) of walls (871). In this regard, protrusions (875, 876) of the present version may bias the corresponding walls (871) toward a substantially vertical orientation by counteracting any laterally-outwardly directed forces that might be applied to walls (871) during use (e.g., clamping and/or firing). In some versions, one or both upper protrusions (875) may be omitted. In some other versions, one or both lower protrusions (876) may be omitted.

VI. EXEMPLARY CARTRIDGE HAVING CARTRIDGE TRAY WITH PROTRUSIONS FOR DECREASING TISSUE GAP

Figure 21:
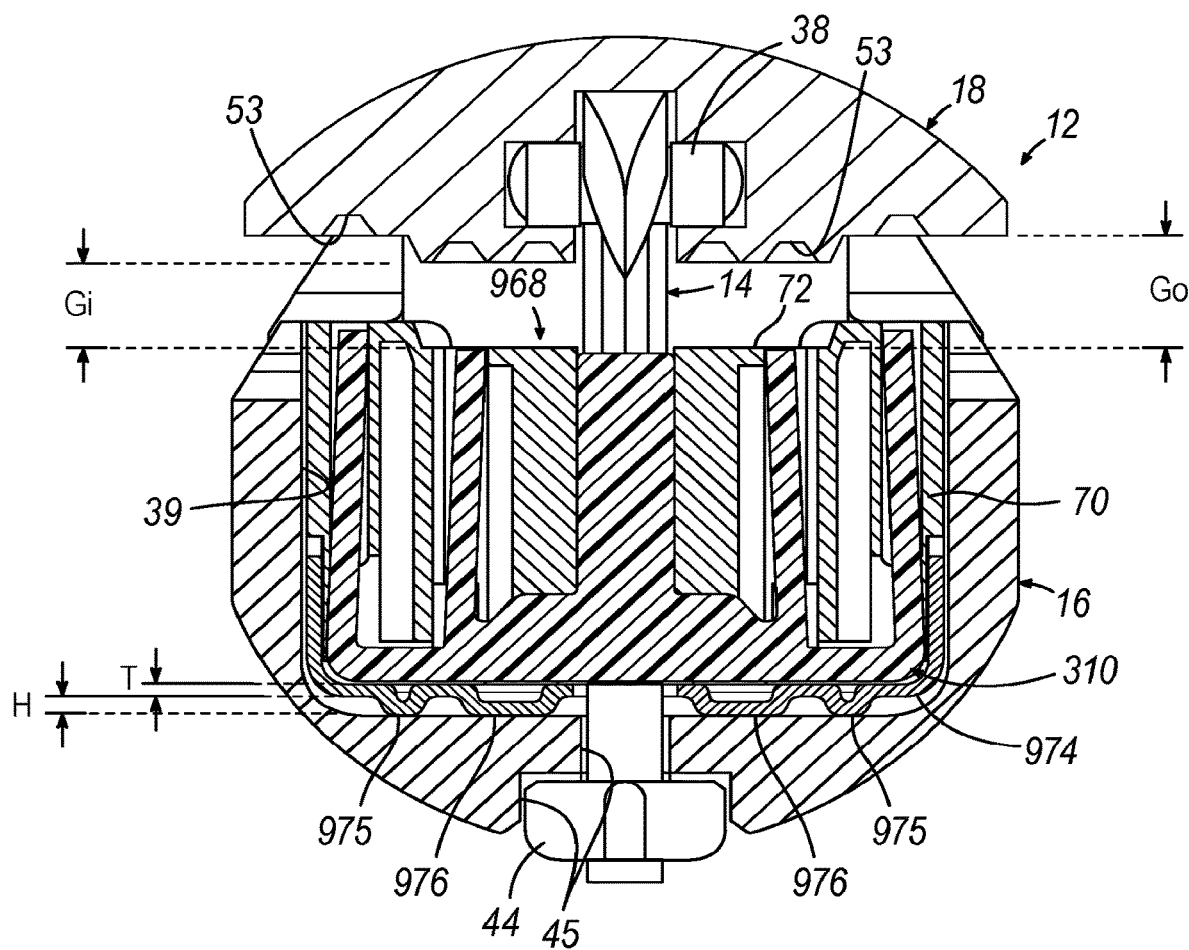
FIG. 21 depicts an end cross-sectional view of the end effector of FIG. 3 with an exemplary staple cartridge removably installed into a channel of a lower jaw of the end effector, showing the staple cartridge having a cartridge tray with protrusions for decreasing a tissue gap between an upper deck of the staple cartridge and an inner surface of the anvil.

In some instances, it may be desirable to provide a staple cartridge that enables a decreased tissue gap between the upper deck of the staple cartridge and the inner surface of anvil (18) having staple forming pockets (53) as compared to staple cartridge (37), to thereby produce more tightly formed staples (47). FIG. 21 shows an exemplary staple cartridge (968) which provides such functionality. Staple cartridge (968) is similar to staple cartridge (37) described above except as otherwise described below. For example, staple cartridge (37) is configured to be removably installed into a channel (39) of lower jaw (16).

As shown, staple cartridge (968) of this example includes cartridge body (70), which is coupled with a lower cartridge tray (974). In the present version, tray (974) includes a laterally-opposed pair of outer protrusions (975) extending downwardly from a lower surface of tray (974), and a laterally-opposed pair of inner protrusions (976) extending downwardly from the lower surface of tray (974). In some versions, protrusions (975, 976) may each have a height (H) relative to the lower surface of tray (974) that is greater than a material thickness (T) of tray (974). For example, protrusions (975, 976) may each have a height (H) relative to the lower surface of tray (974) of approximately 0.010 inch, while tray (974) may have a material thickness (T) of approximately 0.007 inch. Alternatively, any other suitable height of protrusions (975, 976) may be used. In any event, protrusions (975, 976) are configured to abut or otherwise engage an upper surface of channel (39) of lower jaw (16) to thereby vertically support tray (974) above the upper surface of channel (39) of lower jaw (16). For example, protrusions (975, 976) may increase the height of an upper surface of tray (974) (e.g., along which a wedge sled such as wedge sled (310) may translate longitudinally) relative to the upper surface of channel (39) as compared to tray (74) by the height (H) of protrusions (975, 976), thereby also increasing the height of upper deck (72) relative to the upper surface of channel (39) by the height (H) of protrusions (975, 976). Thus, upper deck (72) may be spaced apart from the inner surface of anvil (18) having staple forming pockets (53) by inside and outside tissue gaps (Gi, Go) that are respectively less than those provided in the absence of protrusions (975, 976) by the height (H) of protrusions (975, 976). For example, inside tissue gap (Gi) may be approximately 0.04 inch, and/or outside tissue gap (Go) may be approximately 0.055 inch. In this manner, staple cartridge (968) may cooperate with anvil (18) to produce staples (47) that are more tightly formed as compared to those produced by staple cartridge (37), and that may therefore be capable of clamping tissue more tightly than those produced by staple cartridge (37).

VII. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A staple driver actuator for a surgical stapler comprises: (a) a base having at least one bottom surface, wherein the at least one bottom surface defines a plane, wherein the at least one bottom surface is configured to slide longitudinally relative to a jaw of the surgical stapler; (b) a plurality of rails extending upwardly from the base, wherein each of the plurality of rails includes at least one cam surface, wherein each of the cam surfaces is inclined relative to the plane, wherein the plurality of rails includes: (i) a laterally-opposed pair of outer rails, and (ii) a laterally-opposed pair of inner rails; and (c) a distal nose extending distally from at least a portion of the base and having at least one ledge surface, wherein the at least one ledge surface faces upwardly, is parallel to the plane, and is at least partially positioned distally relative to each of the outer and inner rails.

Example 2

The staple driver actuator of Example 1, wherein the at least one ledge surface includes a laterally-opposed pair of ledge surfaces.

Example 3

The staple driver actuator of any one or more of Examples 1 through 2, wherein the distal nose includes an upper portion and a lower portion extending laterally outwardly relative to the upper portion to define the at least one ledge surface.

Example 4

The staple driver actuator of Example 3, wherein the upper portion is at least partially positioned distally relative to each of the outer and inner rails.

Example 5

The staple driver actuator of any one or more of Examples 1 through 4, wherein the base includes at least one top surface, wherein the at least one ledge surface extends distally from the at least one top surface.

Example 6

The staple driver actuator of any one or more of Example 1 through 5, wherein the base includes at least one top surface, wherein the at least one ledge surface and the at least one top surface are positioned at a same height relative to the plane.

Example 7

The staple driver actuator of any one or more of Examples 1 through 6, wherein the base includes at least one top surface, wherein the at least one ledge surface is seamlessly contiguous with the at least one top surface.

Example 8

The staple driver actuator of any one or more of Examples 1 through 7, wherein the distal nose includes a distal tip, wherein the at least one ledge surface extends distally to the distal tip.

Example 9

The staple driver actuator of any one or more of Example 1 through 7, wherein the at least one ledge surface extends distally to at least one distal cam surface inclined downwardly and distally from the at least one ledge surface toward a distal tip of the distal nose.

Example 10

The staple driver actuator of any one or more of Examples 1 through 9, wherein the distal nose extends upwardly from the base.

Example 11

The staple driver actuator of any one or more of Examples 1 through 10, wherein the distal nose extends distally from the base.

Example 12

The staple driver actuator of any one or more of Examples 1 through 11, wherein the distal nose includes a distal cam surface inclined downwardly and proximally from a distal tip of the distal nose toward the at least one bottom surface.

Example 13

The staple driver actuator of any one or more of Examples 1 through 12, wherein the distal nose is at least partially positioned between the inner rails.

Example 14

The staple driver actuator of Example 13, wherein the distal nose is equally spaced apart from each of the inner rails.

Example 15

An apparatus comprising: (a) a staple cartridge, wherein the staple cartridge includes a cartridge tray and a cartridge body; and (b) the staple driver actuator of any one or more of Examples 1 through 14, wherein the staple driver actuator is captured between the cartridge tray and the cartridge body such that the at least one ledge surface is configured to support at least a portion of the cartridge body.

Example 16

An apparatus comprising: (a) a jaw, wherein the jaw defines a longitudinal axis; (b) an anvil movable relative to the jaw; (c) a cartridge, wherein the cartridge is insertable into the jaw, wherein the cartridge comprises: (i) a plurality of walls, and (ii) a plurality of staple drivers movable relative to the plurality of walls; and (d) a staple driver actuator disposed within the cartridge, wherein the staple driver actuator comprises: (i) a laterally-opposed pair of outer rails configured to cammingly engage respective staple drivers of the plurality of staple drivers during translation of the staple driver actuator along the longitudinal axis, (ii) a laterally-opposed pair of inner rails configured to cammingly engage respective staple drivers of the plurality of staple drivers during translation of the staple driver actuator along the longitudinal axis, and (iii) a distal nose having at least one ledge surface, wherein the at least one ledge surface is at least partially positioned distally relative to each of the outer and inner rails, wherein the at least one ledge surface is configured to support at least one wall of the plurality of walls during translation of the staple driver actuator along the longitudinal axis.

Example 17

The apparatus of Example 16, wherein the distal nose includes an upper portion and a lower portion extending laterally outwardly relative to the upper portion to define the at least one ledge surface.

Example 18

The apparatus of Example 17, wherein the upper portion includes at least one side surface, wherein the at least one side surface is at least partially positioned distally relative to each of the outer and inner rails, wherein the at least one side surface is configured to stabilize the at least one wall of the plurality of walls during translation of the staple driver actuator along the longitudinal axis.

Example 19

The apparatus of any one or more of Examples 16 through 18, wherein the at least one ledge surface includes a laterally-opposed pair of ledge surfaces, wherein the ledge surfaces are configured to support corresponding walls of the plurality of walls during translation of the staple driver actuator along the longitudinal axis.

Example 20

An apparatus comprising: (a) a jaw, wherein the jaw defines a longitudinal axis; (b) an anvil movable relative to the jaw; (c) a cartridge, wherein the cartridge is insertable into the jaw, wherein the cartridge comprises: (i) an elongate slot having a width, and (ii) a plurality of staple drivers movable relative to the elongate slot; and (d) a staple driver actuator disposed within the cartridge, wherein the staple driver actuator comprises: (i) at least one rail configured to cammingly engage the plurality of staple drivers during translation of the staple driver actuator along the longitudinal axis, and (ii) a distal nose having: (A) a lower portion extending to a distal tip of the distal nose, wherein the lower portion is at least partially positioned distally relative to the at least one rail, wherein the lower portion has a first thickness greater than the width of the elongate slot, and (B) an upper portion extending to the distal tip of the distal nose, wherein the upper portion has a second thickness less than or equal to the width of the elongate slot.

VIII. MISCELLANEOUS

Any one or more of the teachings, expressions, embodiments, examples, etc. described herein may be combined with any one or more of the teachings, expressions, embodiments, examples, etc. described in U.S. patent application Ser. No. 17/088,953, entitled "Surgical Stapler End Effector Sled Having Staple Driver Support Feature," filed on Nov. 4, 2020, published as U.S. Pub. No. 2022/0133313 on May 5, 2022, issued as U.S. Pat. No. 11,701,112 on Jul. 18, 2023; U.S. patent application Ser. No. 17/088,961, entitled "Surgical Stapler End Effector Sled Having Tapered Distal End," filed on Nov. 4, 2020, published as U.S. Pub. No. 2022/0133306 on May 5, 2022, issued as U.S. Pat. No. 11,832,814 on Dec. 5, 2023; U.S. patent application Ser. No. 17/088,971, entitled "Surgical Stapler End Effector Sled Having Multiple Surface Finishes," filed on Nov. 4, 2020, published as U.S. Pub. No 2022/0133307 on May 5, 2022, issued as U.S. Pat. No. 11,553,912 on Jan. 17, 2023; U.S. patent application Ser. No. 17/088,982, entitled "Surgical Stapler End Effector Sled Having Cartridge Biasing Feature," filed on Nov. 4, 2020, published as U.S. Pub. No. 2022/0133316 on May 5, 2022; U.S. patent application Ser. No. 29/757,203, entitled "Surgical Stapler End Effector Sled," filed on Nov. 4, 2020; and/or U.S. patent application Ser. No. 29/757,204, entitled "Surgical Stapler End Effector Sled," filed on Nov. 4, 2020. The disclosure of each of these applications is incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Versions of the devices described above may be designed to be disposed of after a single use, or they may be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that may penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention.

Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A staple driver actuator for a surgical stapler, the staple driver actuator comprising:
   (a) a base configured to slide longitudinally relative to a jaw of the surgical stapler, the base including a top surface and a bottom surface; and
   (b) a nose extending upwardly from the base and having a ledge surface raised above the top surface of the base, the nose further having a distal surface extending distally from the ledge surface, the distal surface facing upwards and including a distal-most end spaced above the top surface of the base,
   wherein the distal surface is configured to lift a portion of a staple cartridge body onto the ledge surface as the staple driver actuator advances distally relative to the jaw,
   wherein the ledge surface is configured to support the portion of the staple cartridge body.

2. The staple driver actuator of claim 1, wherein the distal surface comprises a tapered surface inclined downwardly and extending distally from a distal end of the ledge surface.

3. The staple driver actuator of claim 2, wherein the tapered surface is configured to lift the portion of the staple cartridge body onto the ledge surface.

4. The staple driver actuator of claim 3, wherein the portion of the staple cartridge body comprises an inner wall of the staple cartridge body.

5. The staple driver actuator of claim 1, wherein the ledge surface is recessed below a top surface of the nose and extends parallel to the top surface of the base.

6. The staple driver actuator of claim 1, wherein the ledge surface protrudes laterally from a side of the nose.

7. The staple driver actuator of claim 1, wherein the ledge surface includes a smooth surface finish configured to promote reduced friction between the ledge surface and the staple cartridge body, the smooth surface finish being smoother relative to another surface of the nose.

8. The staple driver actuator of claim 7, the distal surface comprising a distal tapered surface inclined downwardly and extending distally from a distal end of the ledge surface, wherein the distal tapered surface includes the smooth surface finish.

9. The staple driver actuator of claim 1, wherein the ledge surface is further configured to engage a lower surface of an inner wall of the staple cartridge body.

10. The staple driver actuator of claim 1, wherein the base includes a raised platform configured to slidably support the staple cartridge body, wherein the ledge surface is seamlessly contiguous with the raised platform and extends distally from the raised platform.

11. The staple driver actuator of claim 10, wherein the raised platform and the ledge surface are configured to slidably support the staple cartridge body without lowering or raising the staple cartridge body as the staple driver actuator advances distally relative to the jaw.

12. The staple driver actuator of claim 1, further comprising a cam surface configured to lift staple drivers housed by the staple cartridge body upwardly as the staple driver actuator advances distally relative to the jaw, wherein the cam surface is positioned proximal to the distal surface such that the staple driver actuator is configured to lift the portion of the staple cartridge body prior to lifting the staple drivers when advanced distally relative to the jaw.

13. The staple driver actuator of claim 1, wherein the ledge surface comprises a first ledge surface, wherein the nose further includes a second ledge surface laterally opposed from the first ledge surface about a central axis of the staple driver actuator, wherein each of the first ledge surface and the second ledge surface includes a distal tapered surface inclined downwardly and extending distally from a distal end of the respective ledge surface.

14. An apparatus comprising:
   (a) a staple cartridge, wherein the staple cartridge includes a cartridge tray and the staple cartridge body; and
   (b) the staple driver actuator of claim 1, wherein the staple driver actuator is captured between the cartridge tray and the staple cartridge body.

15. An apparatus comprising:
   (a) a first jaw, wherein the first jaw defines a longitudinal axis;
   (b) a second jaw having an anvil and movable relative to the first jaw to compress tissue; and
   (c) a staple cartridge insertable into the first jaw, wherein the staple cartridge comprises:
      (i) a cartridge body,
      (ii) a plurality of staple drivers movable within the cartridge body to eject staples into tissue, and
      (iii) a staple driver actuator operable to actuate the staple drivers, wherein the staple driver actuator comprises:
         (A) a base configured to slide longitudinally relative to the first jaw, and
         (B) a central nose extending upwardly from the base, wherein the central nose includes:
            (1) a ledge surface, wherein the ledge surface is configured to support the cartridge body, and
            (2) a distal tapered surface inclined downwardly and extending distally from a distal end of the ledge surface to thereby define a distal point which is a distal-most point of the distal tapered surface, wherein the distal point of the distal tapered surface is raised above a top surface of the base, wherein the distal tapered surface is configured to lift the cartridge body onto the ledge surface as the staple driver actuator advances distally relative to the cartridge body.

16. The staple driver actuator of claim 15, wherein the distal tapered surface is further configured to lift an inner wall of the cartridge body.

* * * * *